US012605532B2

(12) United States Patent
Ito et al.

(10) Patent No.: US 12,605,532 B2
(45) Date of Patent: Apr. 21, 2026

(54) MEDICAL CONNECTOR

(71) Applicant: JMS Co., Ltd., Hiroshima (JP)

(72) Inventors: Maho Ito, Hiroshima (JP); Takaya Fujii, Hiroshima (JP); Hitoshi Tachizaki, Hiroshima (JP); Masahiko Takeuchi, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 484 days.

(21) Appl. No.: 18/262,149

(22) PCT Filed: Jan. 4, 2022

(86) PCT No.: PCT/JP2022/000042
§ 371 (c)(1),
(2) Date: Jul. 19, 2023

(87) PCT Pub. No.: WO2022/163311
PCT Pub. Date: Aug. 4, 2022

(65) Prior Publication Data
US 2024/0082560 A1 Mar. 14, 2024

(30) Foreign Application Priority Data
Feb. 1, 2021 (JP) ................................. 2021-014606

(51) Int. Cl.
*A61M 39/10* (2006.01)

(52) U.S. Cl.
CPC . *A61M 39/1011* (2013.01); *A61M 2039/1033* (2013.01); *A61M 2039/1038* (2013.01)

(58) Field of Classification Search
CPC ...... A61M 39/1011; A61M 2039/1033; A61M 2039/1061
See application file for complete search history.

(56) References Cited

U.S. PATENT DOCUMENTS 9,126,028 B2 9/2015 Fangrow et al.
9,933,094 B2 4/2018 Fangrow
(Continued)

FOREIGN PATENT DOCUMENTS

EP 2 620 178 7/2013
EP 3 081 253 10/2016
(Continued)

OTHER PUBLICATIONS

Extended European Search Report issued in corresponding European Patent Application No. 22745539.1, Nov. 11, 2024, 7 pages.
(Continued)

*Primary Examiner* — Bradley J Osinski
(74) *Attorney, Agent, or Firm* — HSML P.C.

(57) ABSTRACT

A connector (1) is constituted by a first member (10) and a second member (40). The first member (10) has a male connecting portion (11) at a first end and a screwing structure (26) at a second end. The male connecting portion (11) is inserted into a female connecting portion (41) of the second member (40). A first engagement structure (15) is provided on the first member (10), and a second engagement structure (45) is provided on the second member (40) so as to be able to abut against the first engagement structure (15) in the circumferential direction. When a rotational force of a predetermined value or greater is applied to the first member (10) in a tightening direction (R1) of the screwing structure (26), one of the first engagement structure (15) and the second engagement structure (45) is plastically deformed by the other, so that the first member (10) is then rotatable in both forward and reverse directions relative to the second member (40).

12 Claims, 20 Drawing Sheets

(56)                    References Cited

U.S. PATENT DOCUMENTS

| 10,201,693 | B2 | 2/2019 | Tsai |
|---|---|---|---|
| 2013/0144246 | A1 | 6/2013 | Takemoto |
| 2014/0114292 | A1 | 4/2014 | Tachizaki et al. |
| 2016/0354594 | A1* | 12/2016 | Uehara ................. A61M 39/10 |
| 2017/0120032 | A1 | 5/2017 | Miyazaki et al. |
| 2018/0064923 | A1 | 3/2018 | Takeuchi |
| 2019/0321564 | A1* | 10/2019 | Kim ...................... A61M 5/348 |

FOREIGN PATENT DOCUMENTS

| EP | 3 108 926 | 12/2016 |
|---|---|---|
| JP | 56-72659 U | 6/1981 |
| JP | 2001-187990 | 7/2001 |
| JP | 2010-527276 | 8/2010 |
| JP | 2012-254142 | 12/2012 |
| JP | 2013-252165 | 12/2013 |
| JP | 2019-011864 | 1/2019 |
| WO | 02/096500 | 12/2002 |
| WO | 2008/144447 | 11/2008 |
| WO | 2012/002316 | 1/2012 |
| WO | 2013/141137 | 9/2013 |
| WO | 2015/087881 | 6/2015 |
| WO | 2016/133139 | 8/2016 |
| WO | 2016/157974 | 10/2016 |

OTHER PUBLICATIONS

International Search Report issued in International Application No. PCT/JP2022/000042, Mar. 8, 2022, 5 pages w/ translation.
First Office Action issued in corresponding Chinese Office Action issued Jan. 26, 2026, 20 pages w/translation.

* cited by examiner

MEDICAL CONNECTOR

TECHNICAL FIELD

The present invention relates to a medical connector, and more particularly to a connector used in the medical field to form a flow path for a fluid.

BACKGROUND ART

In the medical field, two different members are connected together to form a flow path for a fluid (e.g., a liquid). The two members may be a male connecting portion and a female connecting portion, for example. A continuous flow path is formed between the male connecting portion and the female connecting portion by inserting the male connecting portion into the female connecting portion. There are cases where the two members are provided with respective screwing structures so that the two members connected together can be prevented from separating even when subjected to a pulling force. The screwing structures may be a male thread provided on one of the two members and a female thread provided on the other. The screwing structures are screwed to each other by rotating one of the members relative to the other in a tightening direction of the screwing structures, and then, the screwed state is canceled by rotating the one member in a direction opposite to the tightening direction (loosening direction).

The screwing structures have the following problems.

First, there are cases where, in an attempt to screw the screwing structures to each other, an excessive rotational force acting in the tightening direction is applied to the two members. In such cases, the screwing structures may be damaged.

Second, there are cases where an unintentional rotational force acting in the loosening direction is applied to the two members screwed to each other. In such cases, the screwed connection may be loosened. When the fluid flowing through the two members is a hazardous drug solution (e.g., a drug solution containing an anticancer drug), the hazardous drug solution may leak to the outside, resulting in drug exposure. When the fluid is a bodily fluid (e.g., blood) of a patient, a near-miss event or a medical accident, such as blood leakage, may occur.

Patent Document 1 (FIGS. 63 to 78C) discloses a luer connector 1200 including a first end portion 1212 and a second end portion 1214. The first end portion 1212 constitutes a male connector provided with a female thread 1226. The second end portion 1214 includes a female connecting portion provided with a male thread 1236. The female connecting portion of the second end portion 1214 can be connected to a male connecting portion at a leading end of an injector 1312. The male connecting portion of the injector 1312 includes a female thread that can be screwed to the male thread 1236 of the second end portion 1214. The luer connector 1200 is configured such that, once the injector 1312 is connected to the second end portion 1214 by screwing the female thread of the injector 1312 to the male thread 1236 of the second end portion 1214, the second end portion 1214 can rotate together with the injector 1312 in both forward and reverse directions relative to the first end portion 1212. Therefore, in the state in which the injector 1312 is connected to the second end portion 1214, even if the injector 1312 is further rotated in the tightening direction of the female thread of the injector 1312 relative to the male thread 1236 of the second end portion 1214, the male thread 1236 of the second end portion 1214 and the female thread of the injector 1312 are prevented from being damaged. In addition, even if the injector 1312 is rotated in the opposite direction (loosening direction) to the above rotating direction, the screwed connection between the female thread of the injector 1312 and the male thread 1236 of the second end portion 1214 is prevented from loosening. As such, the luer connector 1200 is configured such that the screwing structures (the male thread 1236 of the second end portion 1214 and the female thread of the injector 1312) of the luer connector 1200 and the injector 1312 do not have the above-described problems.

PRIOR ART DOCUMENTS

Patent Documents

Patent Document 1: JP 2010-527276T
Patent Document 2: WO 2016/133139
Patent Document 3: JP 2013-252165A
Patent Document 4: JP 2012-254142A
Patent Document 5: WO 2013/141137

DISCLOSURE OF INVENTION

Problem to be Solved by the Invention

The second end portion 1214 of the luer connector 1200 of Patent Document 1 includes a first member 1232 including the female connecting portion provided with the male thread 1236 and an annular second member 1234 into which the first member 1232 is inserted. The first member 1232 has a protrusion (tab) 1298 that is engageable with the second member 1234. After the injector 1312 has been connected to the second end portion 1214, rotating the injector 1312 further in the tightening direction shears off the protrusion 1298 and separates the protrusion 1298 from the first member 1232. The first member 1232 is then rotatable in the forward and reverse directions relative to the second member 1234 (and hence the first end portion 1212).

The luer connector 1200 of Patent Document 1 is constituted by a large number of components and has a complex structure, and the assembly thereof is troublesome. Also, the protrusion 1298 separated from the first member 1232 remains in a gap between the first member 1232 and the second member 1234 and can freely move within the gap. Therefore, the protrusion 1298 may obstruct rotation of the first member 1232 relative to the second member 1234.

A first object of the present invention is to provide a medical connector in which, after a rotational force of a predetermined value or greater is applied to a first end of the medical connector, the first end can freely rotate (i.e., idly rotate) relative to a second end of the medical connector. A second object of the present invention is to provide a medical connector that enables idle rotation without generating a broken piece of a member thereof. A third object of the present invention is to provide a medical connector that is constituted by a small number of components, has a simple structure, and is easy to assemble.

Means for Solving Problem

A medical connector of the present invention has a first member and a second member. A male connecting portion is provided at one of a first end of the first member and a first end of the second member. A female connecting portion is provided at the other of the first end of the first member and the first end of the second member. A screwing structure is provided at a second end of the first member. The male connecting portion is inserted into the female connecting portion, and the first member and the second member are in communication with each other. The medical connector includes a dislodgement prevention mechanism that prevents the male connecting portion from dislodging from the female connecting portion, a sealing mechanism that connects the male connecting portion and the female connecting portion to each other in a liquid-tight manner, and a rotation prevention mechanism that prevents the first member from rotating relative to the second member. The rotation prevention mechanism includes a first engagement structure provided on the first member, and a second engagement structure provided on the second member so as to be able to abut against the first engagement structure in a circumferential direction. A direction in which another screwing structure that can be screwed to the screwing structure is rotated in order to screw the other screwing structure to the screwing structure is defined as a tightening direction. The rotation prevention mechanism is configured such that, when a rotational force of a predetermined value or greater is applied to the first member in the tightening direction, one of the first engagement structure and the second engagement structure is plastically deformed by the other, so that the first member can rotate in both forward and reverse directions relative to the second member.

Effects of the Invention

According to the present invention, when a rotational force of a predetermined value or greater acting in the tightening direction is applied to the screwing structure provided at the second end of the first member, one of the first engagement structure and the second engagement structure is plastically deformed. Thus, after that, the first member can rotate (idly rotate) in both the forward and the reverse directions relative to the second member.

One of the first engagement structure and the second engagement structure is plastically deformed. During the plastic deformation, no broken piece occurs. The first member is enabled to idly rotate relative to the second member without generating a broken piece.

The medical connector of the present invention can consist of two components: the first member and the second member. Therefore, the medical connector is constituted by a small number of components, has a simple structure, and is easy to assemble.

DESCRIPTION OF THE INVENTION

Figure 1:
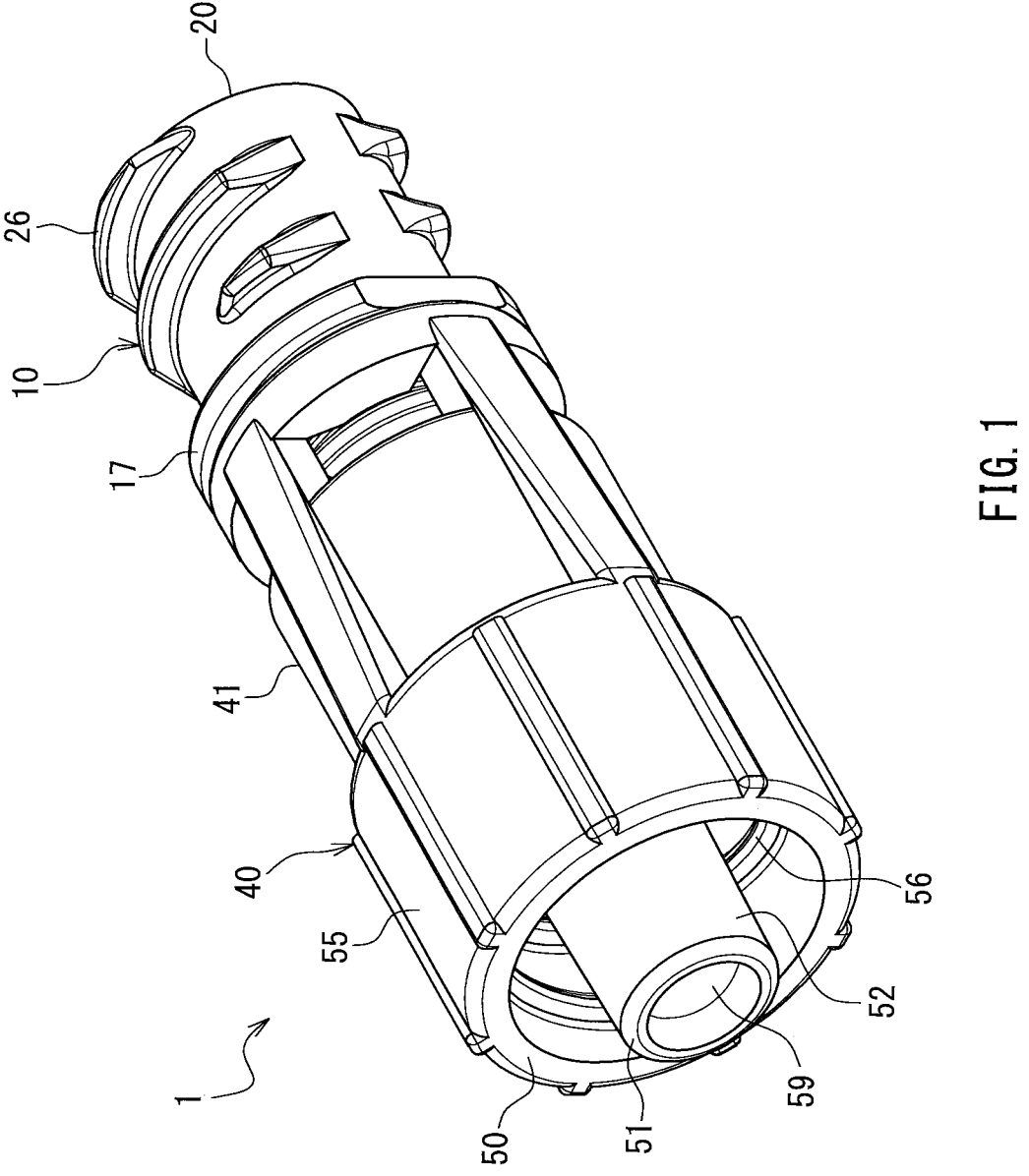
FIG. 1 is a perspective view of a medical connector according to Embodiment 1 of the present invention.

In an aspect of the medical connector of the present invention, both a surface of the first engagement structure and a surface of the second engagement structure that collide with each other when a rotational force acting in the tightening direction is applied to the first member may be flat surfaces that are substantially parallel to a radial direction. According to this aspect, when a rotational force acting in the tightening direction is applied to the first member, the flat surface of the first engagement structure and the flat surface of the second engagement structure abut against each other so as to be in surface contact with each other. This is advantageous in transmitting the rotational force applied to the first member to the second member.

In an aspect of the medical connector of the present invention, one that is to be plastically deformed, of the first engagement structure and the second engagement structure may have a substantially rectangular shape when viewed along the axis of the connector. This aspect is advantageous in transmitting a rotational force acting in the tightening direction applied to the first member to the second member when the rotational force is applied to the first member.

In an aspect of the medical connector of the present invention, one that is to be plastically deformed, of the first engagement structure and the second engagement structure may have a substantially triangular shape when viewed along the axis of the connector. This aspect is advantageous in allowing the first member to idly rotate in the forward and reverse directions relative to the second member, after the plastic deformation.

In an aspect of the medical connector of the present invention, a corner portion of the one that is to be plastically deformed, of the first engagement structure and the second engagement structure may be cut off, the corner portion being located on a side opposite to a side that abuts against the other of the first engagement structure and the second engagement structure when a rotational force acting in the tightening direction is applied to the first member. This aspect is advantageous in allowing the first member to idly rotate in the forward and reverse directions relative to the second member, after the plastic deformation.

In an aspect of the medical connector of the present invention, a surface of the other of the first engagement structure and the second engagement structure may be inclined relative to the circumferential direction, the surface being located on a side opposite to a surface against which the one that is to be plastically deformed, of the first engagement structure and the second engagement structure abuts when a rotational force acting in the tightening direction is applied to the first member. This aspect is advantageous in allowing the first member to idly rotate in a loosening direction (direction that is opposite to the tightening direction) relative to the second member, after the plastic deformation.

In an aspect of the medical connector of the present invention, the female connecting portion may be a first female connecting portion. The second end of the first member may include a tubular second female connecting portion and a male thread provided on an outer circumferential surface of the second female connecting portion. The screwing structure may be the male thread. According to this aspect, the second end of the first member can be connected to a third male connecting portion including a male member that can be inserted into the second female connecting portion and a female thread that can be screwed to the male thread.

In an aspect of the medical connector of the present invention, the male connecting portion may be a first male connecting portion. A second male connecting portion may be provided at the second end of the second member, the second male connecting portion including a male member, an outer cylinder surrounding the male member, and a female thread provided on an inner circumferential surface of the outer cylinder. According to this aspect, the male member at the second end of the first member can be inserted into a tubular third female connecting portion to thereby screw the female thread to a male thread of the third female connecting portion.

In an aspect of the medical connector of the present invention, the male connecting portion may be a first male connecting portion. The female connecting portion may be a first female connecting portion. A second male connecting portion may be provided at one of the second end of the first member and the second end of the second member. A second female connecting portion may be provided at the other of the second end of the first member and the second end of the second member. The second male connecting portion may be interchangeable with a third male connecting portion that is connectable to the second female connecting portion. The second female connecting portion may be interchangeable with a third female connecting portion that is connectable to the second male connecting portion. According to this aspect, the third male connecting portion and the third female connecting portion that are configured to connectable to each other can be connected to each other via the medical connector of the present invention.

In an aspect of the medical connector of the present invention, the male connecting portion may be a first male connecting portion. A second male connecting portion may be provided at the second end of the second member, the second male connecting portion including a male member and a lever that is provided with a claw protruding toward the male member and is configured to be elastically rotatable so that the claw can move away from the male member. According to this aspect, the second male connecting portion at the second end of the second member can be connected to a female port portion including a septum into which the male member can be inserted and an engagement portion with which the claw can engage.

In an aspect of the medical connector of the present invention, the rotational force of the predetermined value or greater may be 0.08 N·m or greater. This aspect is advantageous in connecting the second end of the first member or the second end of the second member of the medical connector of the present invention to another member in a liquid-tight manner.

In an aspect of the medical connector of the present invention, each of the first member and the second member may be a single component made entirely of one material. This aspect is advantageous in reducing the number of components constituting the medical connector of the present invention, simplifying the structure of the connector, and facilitating assembly of the connector.

Hereinafter, the present invention will be described in detail while showing preferred embodiments thereof. However, it goes without saying that the present invention is not limited to the embodiments below. In the drawings that will be referred to in the following description, only the main members of constituent members of the embodiments of the present invention are shown in a simplified manner for the sake of convenience of description. Accordingly, the present invention may include optional members that are not shown in the drawings below. Moreover, it should be understood that the members shown in the drawings below may be modified or omitted within the scope of the present invention. In the drawings that will be referred to in the description of the embodiments below, members corresponding to those members shown in the drawings that are referred to in the description of any preceding embodiment are denoted by the same reference numerals as the reference numerals of the members shown in the drawings of that preceding embodiment. With respect to such members, redundant descriptions are omitted, and the description of the preceding embodiment should be appropriately taken into account.

In the present invention, the "axis" of a member (e.g., a connector, a first member, a second member, a male connecting portion, or a female connecting portion) means the central axis of that member. The "axis" passes through the center of a circle contained in the member and/or coincides with the central axis of a cylinder or cone (taper) contained in the member. For the sake of simplicity of the drawings, axes are omitted from the drawings. A direction along a straight line orthogonal to an axis is referred to as "radial direction". With respect to the radial direction, the side nearer to the axis is referred to as "inner" side, and the side farther from the axis is referred to as "outer" side. A direction of rotation about the axis is referred to as "circumferential direction".

Embodiment 1

Figure 2:
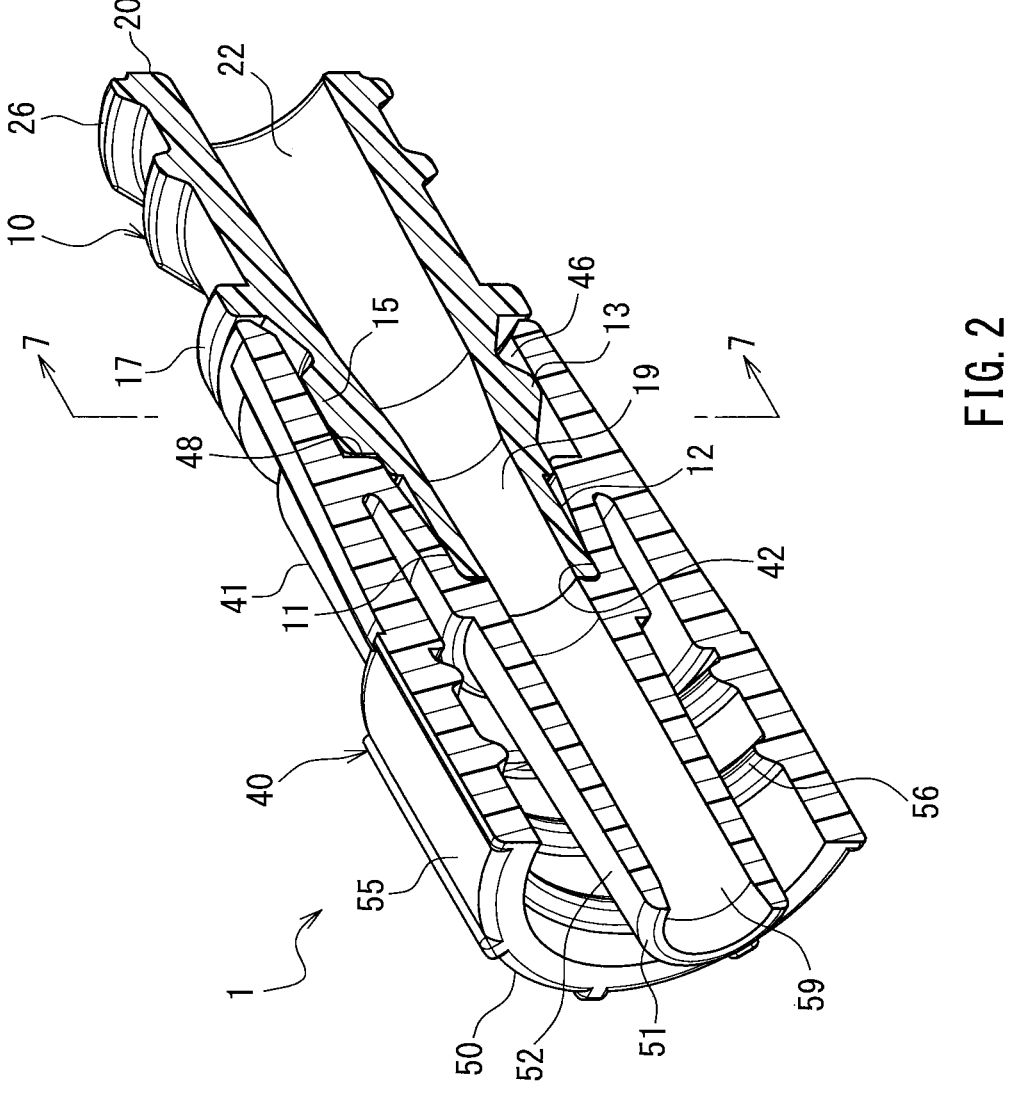
FIG. 2 is a perspective cross-sectional view of the medical connector according to Embodiment 1 of the present invention.
Figure 3:
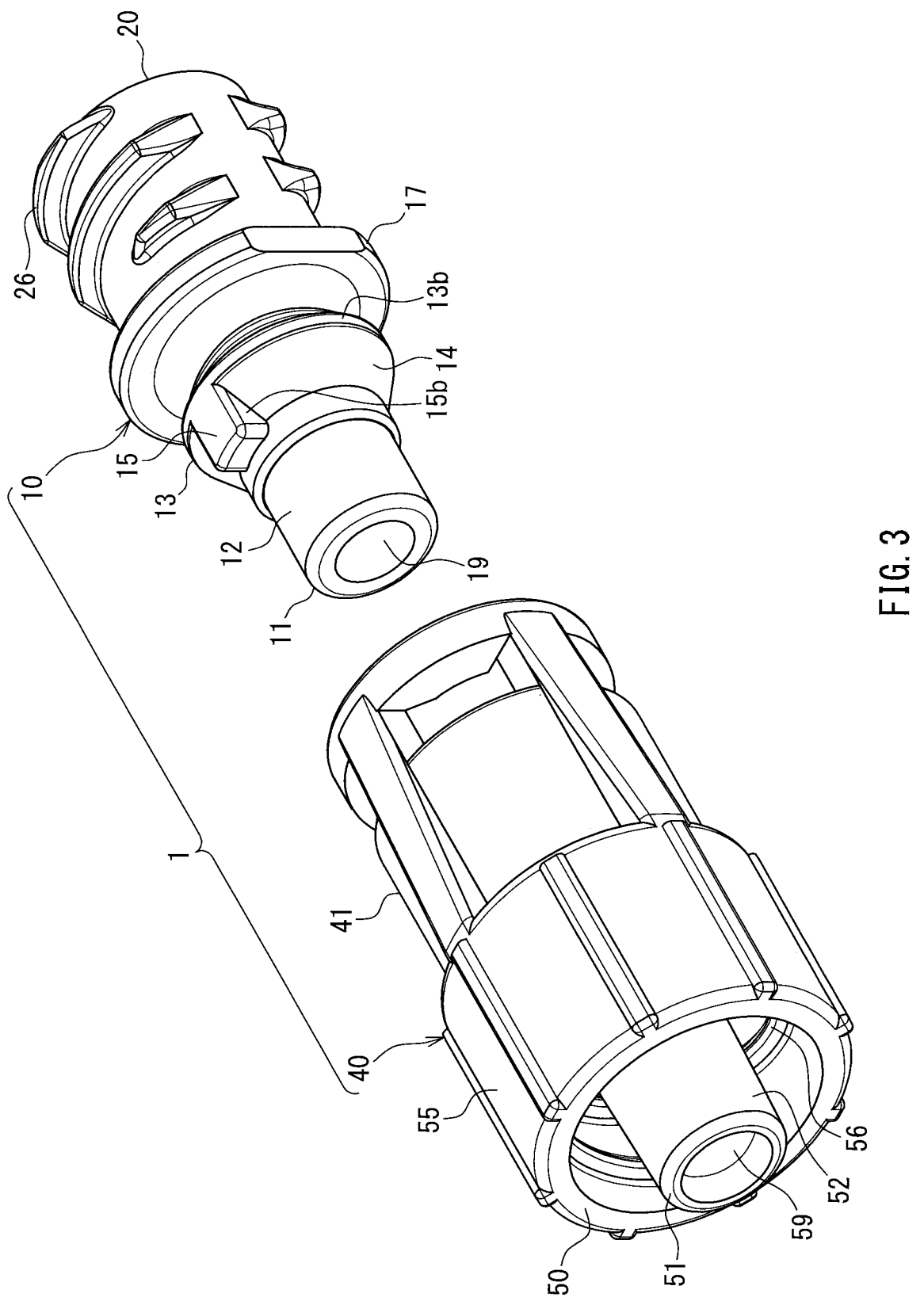
FIG. 3 is an exploded perspective view of the medical connector according to Embodiment 1 of the present invention.
Figure 4:
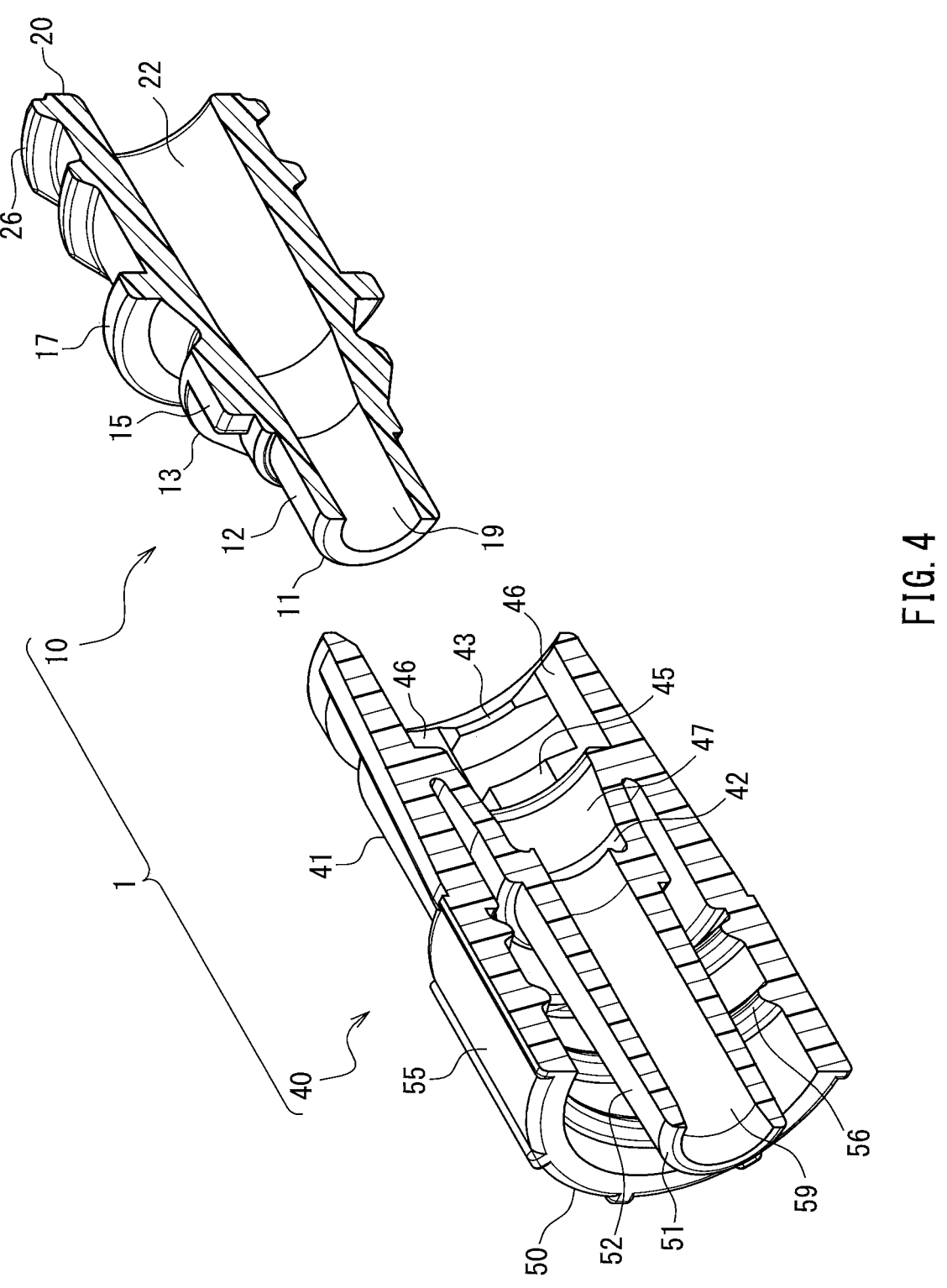
FIG. 4 is an exploded perspective cross-sectional view of the medical connector according to Embodiment 1 of the present invention.

FIG. 1 is a perspective view of a medical connector (hereinafter referred to simply as "connector") 1 according to Embodiment 1 of the present invention. FIG. 2 is a perspective cross-sectional view of the connector 1. FIG. 3 is an exploded perspective view of the connector 1, and FIG. 4 is an exploded perspective cross-sectional view of the connector 1. The connector 1 is constituted by a first member 10 and a second member 40.

Now, the first member 10 will be described. As shown in FIGS. 3 and 4, the entire first member 10 has a hollow tubular shape. A flow path 19 extends through the first member 10 along the axis of the first member 10. The first member 10 has a male connecting portion (first male connecting portion) 11 at a first end and a female connecting portion (second female connecting portion) 20 at a second end, the female connecting portion 20 being coaxial with the male connecting portion 11.

The male connecting portion 11 has a substantially cylindrical shape. The male connecting portion 11 has, on its outer circumferential surface, a first sealing surface 12 and an annular rib 13 in this order from a distal end of the male connecting portion 11 toward the female connecting portion 20. The first sealing surface 12 is a cylindrical surface whose outer diameter is constant in the axial direction, or a male tapered surface (conical surface) whose outer diameter gradually decreases toward the distal end of the male connecting portion 11. The annular rib 13 is a protrusion protruding radially outward and is continuous in the circumferential direction. The annular rib 13 has, on the first sealing surface 12 side with respect to a top portion (the most protruding portion protruding radially outward) 13a thereof, a tapered surface (conical surface) 14 whose outer diameter gradually decreases toward the first sealing surface 12. An engagement protrusion 15 is provided on the first sealing surface 12 side with respect to the top portion 13a of the annular rib 13. The engagement protrusion 15 protrudes radially outward from the tapered surface 14 of the annular rib 13, and extends from the top portion 13a of the annular rib 13 toward the first sealing surface 12 in the axial direction. The engagement protrusion 15 has a substantially rectangular shape when viewed from the male connecting portion 11 side along the axis of the first member 10.

The female connecting portion 20 also has a substantially cylindrical shape. An outer circumferential surface of the female connecting portion 20 is a cylindrical surface, and a male thread 26 is provided on the outer circumferential surface. The male thread 26 is a right-hand thread. An inner circumferential surface of the female connecting portion 20 has a female tapered surface (e.g., a 6% tapered surface) 22 whose inner diameter gradually increases toward a distal end of the female connecting portion 20. The female connecting portion 20 (in particular, the female tapered surface 22 and the male thread 26) may comply with ISO 594-2 or ISO 80369-7, for example.

The first member 10 has a flange 17 between the male connecting portion 11 and the female connecting portion 20. The flange 17 is a protrusion that protrudes radially outward from an outer circumferential surface of the first member 10.

The flange 17 is positioned while being slightly spaced apart from the annular rib 13 toward the female connecting portion 20. In Embodiment 1, the flange 17 is continuous in the circumferential direction; however, the present invention is not limited to this configuration. The flange 17 may be discontinuous in the circumferential direction, and, for example, may be a pair of protrusions (including ribs) that protrude radially outward and are arranged symmetrically with respect to the axis of the first member 10.

Now, the second member 40 will be described. As shown in FIGS. 3 and 4, the second member 40 has a female connecting portion (first female connecting portion) 41 at a first end and a male connecting portion (second male connecting portion) 50 at a second end, the male connecting portion 50 being coaxial with the female connecting portion 41.

Figure 5:
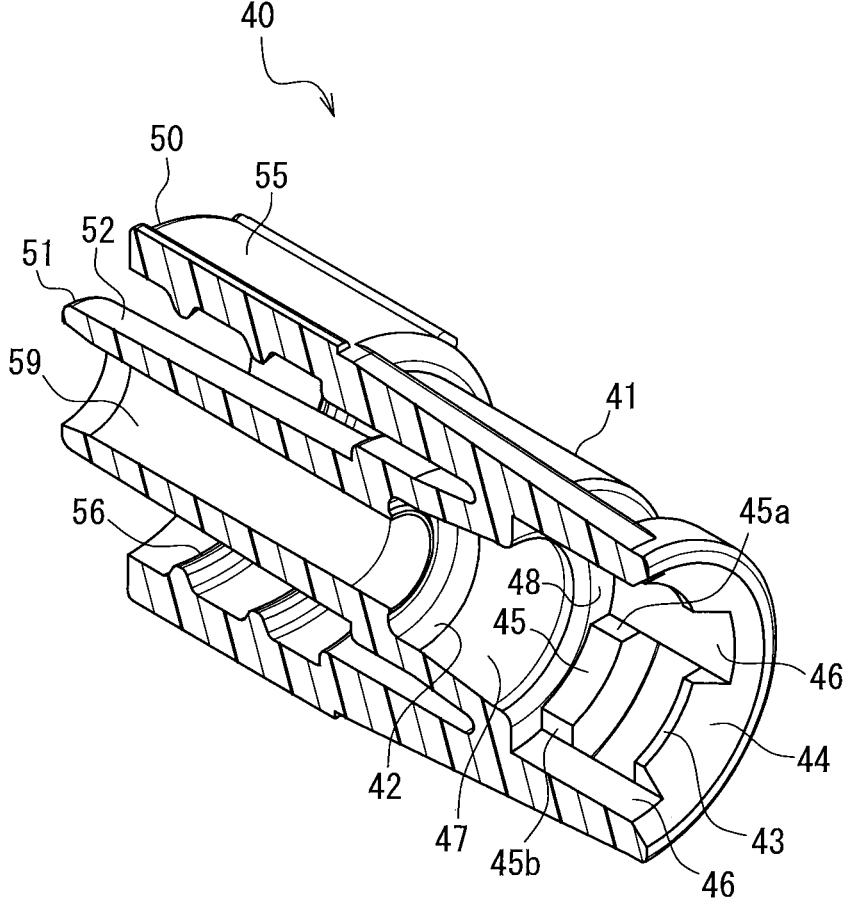
FIG. 5 is a cross-sectional perspective view of a second member constituting the medical connector according to Embodiment 1 of the present invention, when viewed from a female connecting portion side.

The female connecting portion 41 has a substantially hollow cylindrical shape. FIG. 5 is a cross-sectional perspective view of the second member 40 when viewed from the female connecting portion 41 side. The female connecting portion 41 has, on its inner circumferential surface, a first rib 43, a second rib 45, and a second sealing surface 42 in this order from a distal end of the female connecting portion 41 toward the male connecting portion 50.

The first rib 43 is provided near the distal end of the female connecting portion 41 (or an opening end of the female connecting portion 41). The first rib 43 has, on a side nearer to the distal end of the female connecting portion 41 with respect to a top portion (the most protruding portion protruding radially inward) of the first rib 43, a tapered surface (conical surface) 44 whose inner diameter gradually increases toward the distal end of the female connecting portion 41. The second rib 45 is positioned on the male connecting portion 50 side with respect to the first rib 43 while being slightly spaced apart from the first rib 43. Each of the first rib 43 and the second rib 45 extends in the circumferential direction. Furthermore, grooves 46 are formed in the inner circumferential surface of the female connecting portion 41. The grooves 46 extend parallel to the axis of the second member 40 such that the grooves 46 traverse the first rib 43 and the second rib 45. In other words, the grooves 46 divide the first rib 43 in the circumferential direction and divide the second rib 45 in the circumferential direction. The grooves 46 each have a substantially rectangular shape when viewed from the female connecting portion 41 side along the axis of the second member 40. In Embodiment 1, four grooves 46 are arranged equiangularly around the axis of the second member 40. As a result, the first rib 43 and the second rib 45 are each divided into four sections in the circumferential direction. In the present invention, any number of grooves 46 may be provided, and the number may be one or more. Note that a plurality of grooves 46 do not need to be arranged equiangularly around the axis of the second member 40, and may be irregularly arranged.

The second sealing surface 42 is a cylindrical surface whose inner diameter is constant in the axial direction, or a female tapered surface (conical surface) whose inner diameter gradually increases toward the distal end of the female connecting portion 41. A guide surface 47 is provided adjacent to the second sealing surface 42 on the second rib 45 side of the second sealing surface 42. The guide surface 47 is a conical surface whose inner diameter gradually increases toward the distal end of the female connecting portion 41. A bottom surface (surface that opposes the axis of the second member 40) of each groove 46 is located radially outward of the guide surface 47. Thus, there is a step surface 48 between the guide surface 47 and the groove 46, the step surface 48 being formed due to the difference in inner diameter between the guide surface 47 and the groove 46. The step surface 48 is a flat surface that is parallel to the radial direction. The grooves 46 terminate at the step surface 48. The second rib 45 protrudes from the step surface 48 toward the distal end (or the first rib 43) of the female connecting portion 41.

The male connecting portion 50 has a male member 51 having a hollow cylindrical shape and an outer cylinder 55 surrounding the male member 51 (see FIGS. 3 and 4). A flow path 59 is provided in the male member 51 and extends through the male member 51 along the axis of the male member 51. The flow path 59 is in communication with an inner cavity of the female connecting portion 41 (in particular, the second sealing surface 42 and the guide surface 47). An outer circumferential surface of the male member 51 has a male tapered surface (e.g., a 6% tapered surface) 52 whose outer diameter gradually decreases toward a distal end of the male member 51. The outer cylinder 55 has a substantially cylindrical shape and is disposed coaxially with the male member 51 while being spaced apart from the male member 51 in the radial direction. A female thread 56 is provided on an inner circumferential surface of the outer cylinder 55 that opposes the male member 51. The female thread 56 is a right-hand thread. The male connecting portion 50 (in particular, the male tapered surface 52 and the female thread 56) may comply with ISO 594-2 or ISO 80369-7, for example.

The first member 10 and the second member 40 are preferably made of a resin material, although there are no limitations. Examples of resin materials that can be used for the first member 10 and the second member 40 include resin materials such as polycarbonate, polypropylene, polyacetal, polyamide, hard polyvinyl chloride, polyethylene, styrene-ethylene, polyethylene terephthalate, polybutylene terephthalate, a butylene-styrene block copolymer, and the like. The material of the first member 10 and the material of the second member 40 may be the same or different. When the first member 10 and the second member are made of the same material, the material of the first and second members 10 and 40 preferably has toughness. For example, the first and second members 10 and 40 can be made of polypropylene. When the first member 10 and the second member are made of different materials, the material of the first member 10 preferably has toughness, and the material of the second member 40 is preferably stronger (or harder) than the material of the first member 10. For example the first member 10 can be made of polypropylene, and the second member 40 can be made of polycarbonate. It is preferable that each of the first member 10 and the second member 40 is integrally produced as a single component made entirely of one material through injection molding using an aforementioned resin material.

The connector 1 is assembled by inserting the male connecting portion 11 of the first member 10 into the female connecting portion 41 of the second member 40. More specifically, as shown in FIGS. 3 and 4, the male connecting portion 11 is placed coaxially with and facing the female connecting portion 41. At this time, the first member 10 is aligned with the second member 40 in the circumferential direction so that the engagement protrusion 15 of the male connecting portion 11 matches one of the grooves 46 (see FIG. 5) of the female connecting portion 41. Since a plurality of grooves 46 are provided in the female connecting portion 41, it is easy to align the first member 10 with the second member 40 in the circumferential direction. Then, the first member 10 is pushed into the second member 40.

The outer diameter of the annular rib 13 of the male connecting portion 11 is larger than the inner diameter of the first rib 43 of the female connecting portion 41. The tapered surface 14 of the annular rib 13 abuts against the tapered surface 44 of the first rib 43 in the axial direction. Strongly pushing the first member 10 into the second member 40 slightly deforms the male connecting portion 11 and/or the female connecting portion 41, and the annular rib 13 moves over the first rib 43. In this manner, the connector 1 can be assembled, as shown in FIGS. 1 and 2.

Figure 6:
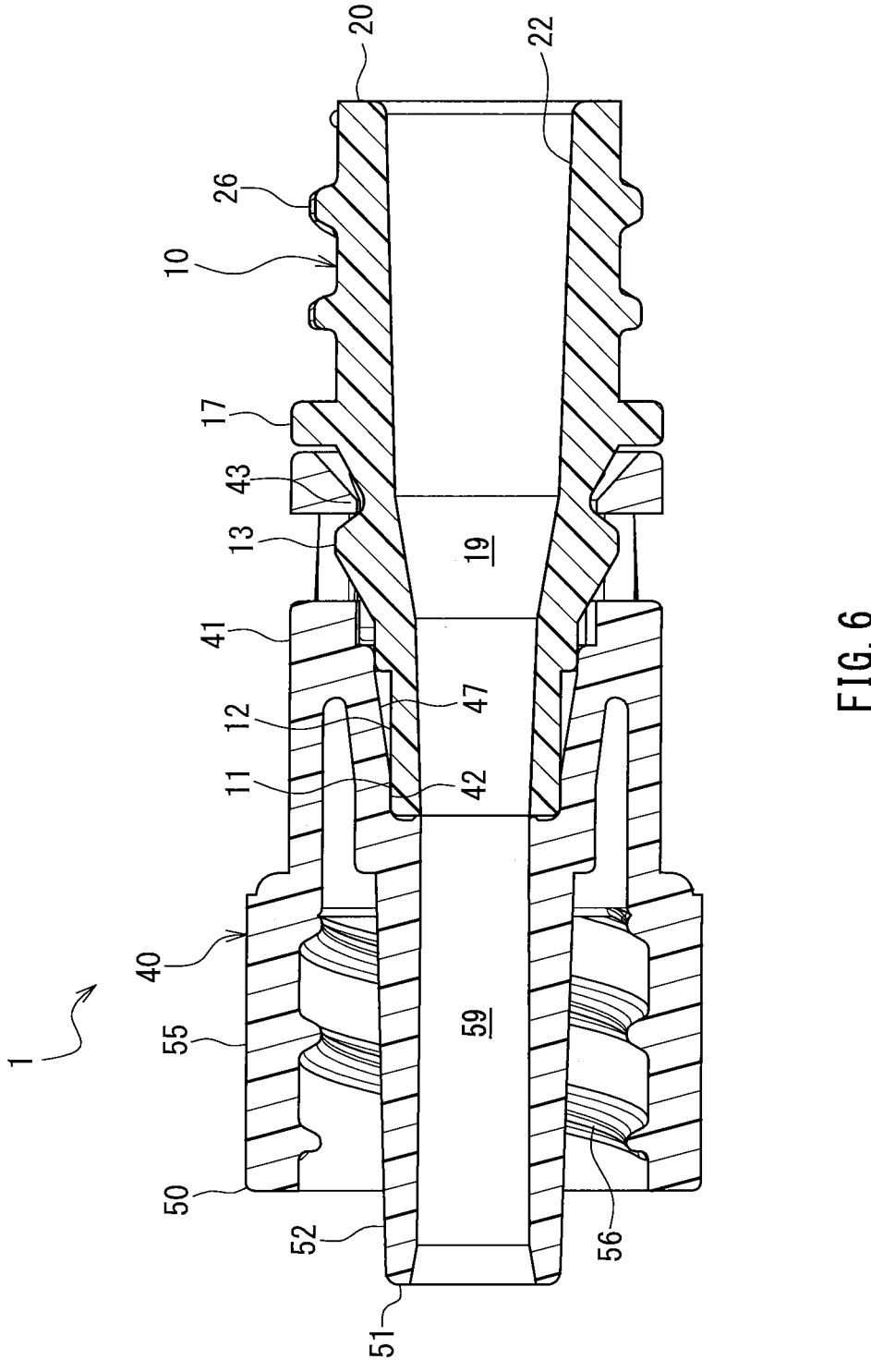
FIG. 6 is a cross-sectional view of the medical connector according to Embodiment 1 of the present invention, taken along a plane containing an axis thereof.

FIG. 6 is a cross-sectional view of the connector 1. The cross section shown in FIG. 6 is rotated by 45 degrees about the axis of the connector 1 relative to the cross section shown in FIG. 2. As shown in FIG. 6, the annular rib 13 of the male connecting portion 11 opposes the first rib 43 of the female connecting portion 41 in the axial direction and is in the vicinity of (or abuts against) the first rib 43 (i.e., the annular rib 13 is engaged with the first rib 43). Therefore, once the male connecting portion 11 is inserted into the female connecting portion 41, it is difficult to separate the first member 10 from the second member 40. The male connecting portion 11 is irreversibly inserted into the female connecting portion 41. The annular rib 13 and the first rib 43 constitute a "dislodgement prevention mechanism" that prevents the male connecting portion 11 from dislodging from the female connecting portion 41 in the axial direction.

The first sealing surface 12 of the male connecting portion 11 is fitted into the second sealing surface 42 of the female connecting portion 41. The first sealing surface 12 and the second sealing surface 42 are in surface contact with each other to form a liquid-tight seal therebetween. The first sealing surface 12 and the second sealing surface 42 constitute a "sealing mechanism" that connects the male connecting portion 11 and the female connecting portion 12 to each other in a liquid-tight manner. The flow path 19 of the first member 10 (or the male connecting portion 11) and the flow path 59 of the second member 40 (or the male connecting portion 50) are in communication with each other. This sealing mechanism prevents a fluid (e.g., a liquid) that flows through the flow paths 19 and 59 from leaking to the outside through between the first sealing surface 12 and the second sealing surface 42. The liquid-tight seal between the first sealing surface 12 and the second sealing surface 42 is maintained even when the first member 10 rotates (described in detail later) relative to the second member 40. The guide surface 47 of the female connecting portion 41 guides the male connecting portion 11 (in particular, the first sealing surface 12 thereof) to the second sealing surface 42 of the female connecting portion 41 during the process of assembling the connector 1.

Figure 7:
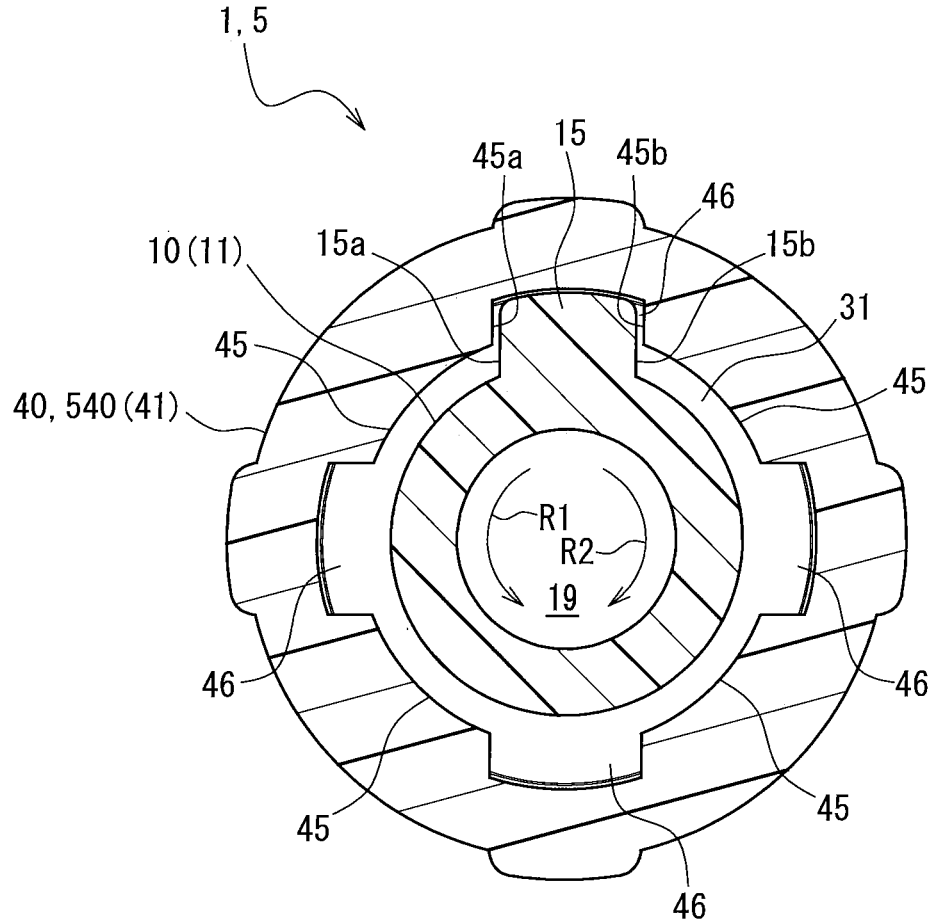
FIG. 7 is a cross-sectional view of the medical connector according to Embodiment 1 of the present invention, taken along a plane containing line 7-7 in FIG. 2.

FIG. 7 is a cross-sectional view of the connector 1 taken along a plane containing line 7-7 in FIG. 2 (a plane that passes through the engagement protrusion and is perpendicular to the axis of the connector 1). The engagement protrusion (see FIGS. 3 and 4) of the male connecting portion 11 is fitted into one of the grooves 46 (see FIG. 5) of the female connecting portion 41. Side surfaces (surfaces facing in the circumferential direction) 15a and 15b of the engagement protrusion 15 oppose and are located in the vicinity of (or abut against) corresponding side surfaces (surfaces facing in the circumferential direction, which also are side surfaces of the groove 46) 45a and 45b of two of the divided sections of the second rib 45 that are adjacent to each other in the circumferential direction. When an attempt is made to rotate the first member 10 about its axis relative to the second member 40 in either the direction indicated by arrow R1 or the direction indicated by arrow R2, the engagement protrusion 15 abuts against the second rib 45 in the circumferential direction, and the rotation of the first member 10 relative to the second member 40 is stopped. The engagement protrusion 15 and the second rib 45, which are provided so as to be able to abut against each other in the circumferential direction, constitute the "rotation prevention mechanism" that prevents the first member 10 from rotating relative to the second member 40. As shown in FIG. 2, the engagement protrusion 15 opposes the step surface 48 of the female connecting portion 41 in the axial direction and is in the vicinity of (or abuts against) the step surface 48.

Figure 8:
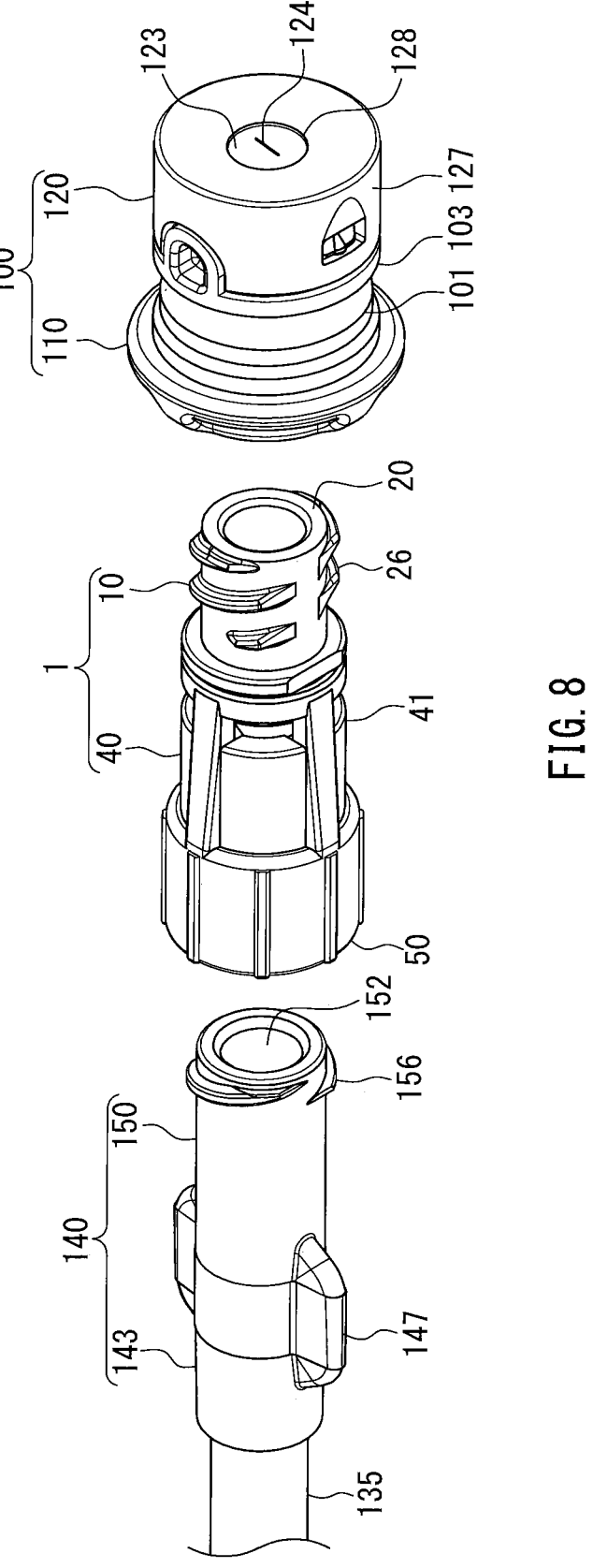
FIG. 8 is an exploded perspective view illustrating an example method of using the medical connector according to Embodiment 1 of the present invention.
Figure 9:
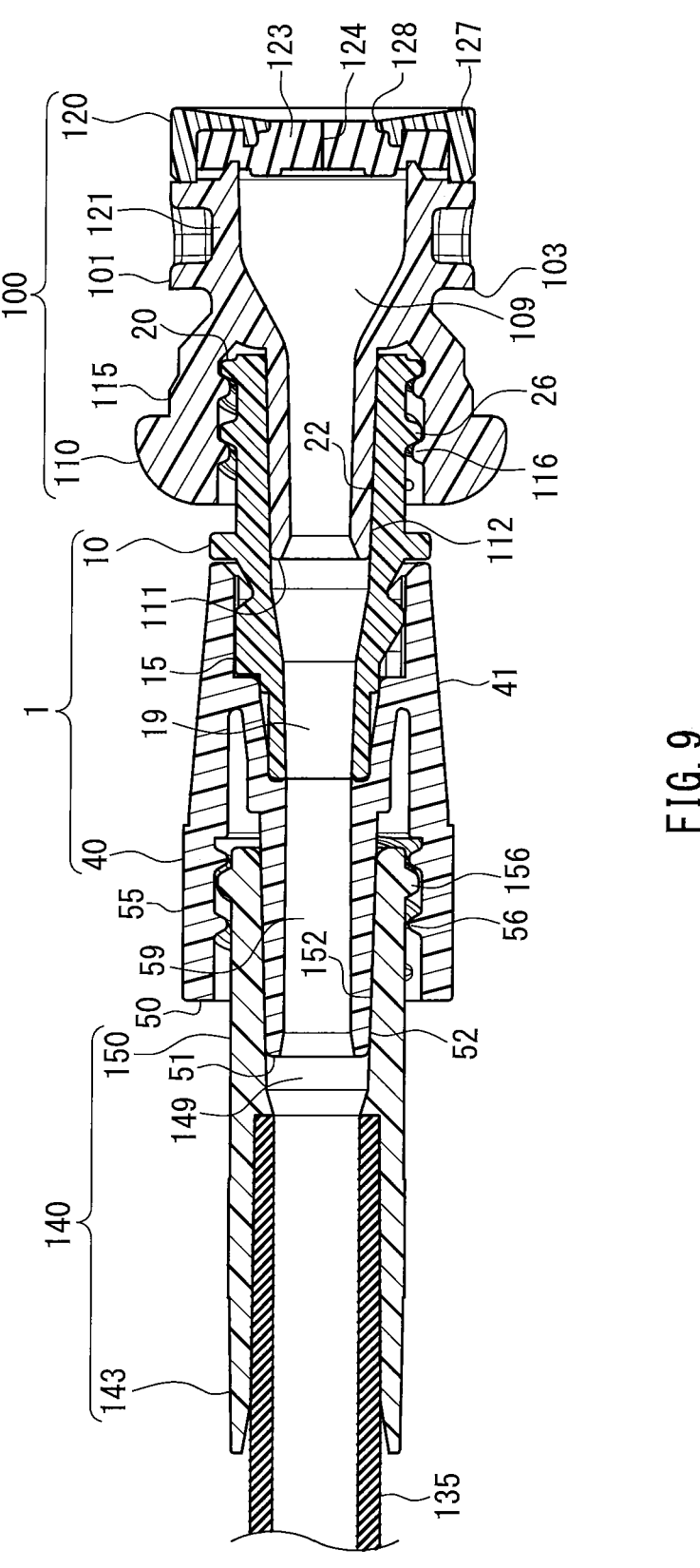
FIG. 9 is a cross-sectional view illustrating the example method of using the medical connector according to Embodiment 1 of the present invention.

FIG. 8 is an exploded perspective view illustrating an example method of using the connector 1. The connector 1 can be used to connect a female plug 100 and a tube member 140 via the connector 1 provided therebetween. FIG. 9 is a cross-sectional view showing a state in which the female plug 100 and the tube member 140 are connected to each other via the connector 1.

The female plug 100 has a male connecting portion (third male connecting portion) 110 at a first end and a female port portion 120 at a second end, the female port portion 120 being coaxial with the male connecting portion 110. As shown in FIG. 9, the female plug 100 is constituted by a plug main body 101, a partition member (hereinafter referred to as "septum") 123, and a cap 127.

The plug main body 101 has a male member 111 and an outer cylinder 115 on the male connecting portion 110 side, and a base 121 on the female port portion 120 side. A flow path 109 extends through the plug main body 101 along the axis of the female plug 100. The male member 111 and the base 121 are in communication with each other via the flow path 109.

The male connecting portion 110 has the male member 111 having a hollow cylindrical shape and the outer cylinder 115 surrounding the male member 111. The flow path 109 extends through the male member 111. An outer circumferential surface of the male member 111 has a male tapered surface (e.g., a 6% tapered surface) 112 whose outer diameter gradually decreases toward a distal end of the male member 111. The outer cylinder 115 has a substantially cylindrical shape and is disposed coaxially with the male member 111 while being spaced apart from the male member 111 in the radial direction. A female thread 116 is provided on an inner circumferential surface of the outer cylinder 115 that opposes the male member 111. The female thread 116 is a right-hand thread. The male connecting portion 110 (in particular, the male tapered surface 112 and the female thread 116) may comply with ISO 594-2 or ISO 80369-7, for example. The male connecting portion 110 is interchangeable with the male connecting portion 50 (see FIGS. 1 to 4) of the connector 1.

The female port portion 120 is constituted by the base 121 of the plug main body 101, the septum 123, and the cap 127. The base 121 has a substantially cylindrical shape. An inner cavity of the base 121 is in communication with the flow path 109. The septum 123 is provided at a distal end of the base 121 so as to close the flow path 109. The cap 127 covers the septum 123 and is fixed to the plug main body 101 (in particular, the base 121 thereof.

The septum 123 has a circular thin plate-like shape. A straight line-shaped slit (cut) 124 penetrating the septum 123 in its thickness direction is formed at the center of the septum 123. The septum 123 is made of an elastic (or flexible) soft material (so-called elastomer) so that it can be relatively easily deformed by an external force and immediately return to a state before deformation (initial state) when the external force is removed. Examples of soft materials that can be used include, but are not limited to, soft polyvinyl chloride, thermoplastic elastomers (e.g., styrene-based elastomers, olefin-based elastomers, polyurethane-based elastomers, etc.), and rubbers (e.g., isoprene rubber, silicone rubber, butyl rubber, etc.). The entire septum 123 can be integrally produced as a single component using an aforementioned material. An opening 128 is formed at the center of a top plate of the cap 127. The slit 124 of the septum 123 is exposed to the outside via the opening 128. FIGS. 8 and 9 show the septum 123 in the initial state. In the initial state, the slit 124 is closed in a liquid-tight manner.

It is preferable that the plug main body 101 and the cap 127 are made of a hard material. Specifically, a resin material such as polyacetal, polycarbonate, polystyrene, polyamide, polypropylene, or rigid polyvinyl chloride may be used. The entire plug main body 101 and the entire cap 127 can each be integrally produced as a single component through injection molding or the like using an aforementioned resin material.

The female plug 100 including the septum 123 in which the slit 124 is formed is known from Patent Document 2 (FIGS. 10A and 10B) and Patent Document 3, for example.

The tube member 140 has a female connecting portion (third female connecting portion) 150 at a first end and a base end portion 143 at a second end, the base end portion 143 being coaxial with the female connecting portion 150. The entire tube member 140 has a hollow tubular shape. A flow path 149 extends through the tube member 140 along the axis (not shown) of the tube member 140. The female connecting portion 150 and the base end portion 143 are in communication with each other via the flow path 149.

The female connecting portion 150 has a substantially cylindrical shape. An outer circumferential surface of the female connecting portion 150 is a cylindrical surface, and a male thread 156 is provided on the outer circumferential surface. The male thread 156 is a right-hand thread. An inner circumferential surface of the female connecting portion 150 has a female tapered surface (e.g., a 6% tapered surface) 152 whose inner diameter gradually increases toward a distal end of the female connecting portion 150. The female connecting portion 150 (in particular, the female tapered surface 152 and the male thread 156) may comply with ISO 594-2 or ISO 80369-7. The female connecting portion 150 is interchangeable with the female connecting portion 20 (see FIGS. 1 to 4) of the connector 1.

The base end portion 143 also has a substantially cylindrical shape. A flexible tube 135 is inserted into the base end portion 143 and fixed to the base end portion 143 using an adhesive or the like. The tube 135 is in communication with the flow path 149 of the tube member 140. Another end, which is not shown, of the tube 135 may be connected to, for example, an infusion circuit for infusion to a patient, although there are no limitations.

A plurality of (two in Embodiment 1) protrusions 147 protrude radially outward from an outer circumferential surface of the tube member 140. The protrusions 147 facilitate application of a rotational force to the tube member 140.

It is preferable that the tube member 140 is made of a hard material. Specifically, a resin material such as polyacetal, polycarbonate, polystyrene, polyamide, polypropylene, or rigid polyvinyl chloride may be used. The entire tube member 140 can be integrally produced as a single compo-
nent through injection molding or the like using an afore-
mentioned resin material.

As shown in FIGS. 8 and 9, the connector 1 is used to
connect the female plug 100 to the tube member 140.

The male connecting portion 110 of the female plug 100
is inserted into the female connecting portion 20 of the first
member 10 of the connector 1. More specifically, the male
member 111 of the male connecting portion 110 is inserted
into the female connecting portion 20. The female connect-
ing portion 20 is inserted into a gap between the male
member 111 and the outer cylinder 115 of the male con-
necting portion 110. The female thread 116 of the male
connecting portion 110 is screwed to the male thread 26 of
the female connecting portion 20 by rotating the female plug
100 relative to the first member 10. The male tapered surface
112 of the male member 111 comes into surface contact with
the female tapered surface 22 of the female connecting
portion 20, and thus, the two tapered surfaces are taper-fitted
to each other. The screwed connection of the female thread
116 to the male thread 26 prevents unintentional separation
of the male connecting portion 110 from the female con-
necting portion 20 even when a pulling force is applied.

The female connecting portion 150 of the tube member
140 is connected to the male connecting portion 50 of the
second member 40 of the connector 1. More specifically, the
male member 51 of the male connecting portion 50 is
inserted into the female connecting portion 150. The female
connecting portion 150 is inserted into a gap between the
male member 51 and the outer cylinder 55 of the male
connecting portion 50. The female thread 56 of the male
connecting portion 50 is screwed to the male thread 156 of
the female connecting portion 150 by rotating the second
member relative to the tube member 140. The male tapered
surface 52 of the male member 51 comes into surface
contact with the female tapered surface 152 of the female
connecting portion 150, and thus, the two tapered surfaces
are taper-fitted to each other. The screwed connection of the
female thread 56 to the male thread 156 prevents uninten-
tional separation of the male connecting portion 50 from the
female connecting portion 150 even when a pulling force is
applied.

Thus, the female plug 100 (flow path 109), the connector
1 (flow paths 19 and 59), the tube member 140 (flow path
149), and the tube 135 are sequentially in communication
with each other. A male member (see Patent Documents 2
and 3, for example) without a sharp tip can be connected to
the female port portion 120 (in particular, the slit 124 of the
septum 123) of the female plug 100 to allow the fluid to flow
through the male member, the female plug 100, the connec-
tor 1, the tube member 140, and the tube 135 in this order
or in reverse order.

Effects of the connector 1 of Embodiment 1 will be
described.

As described above, the male connecting portion 50 of the
connector 1 is interchangeable with the male connecting
portion 110 of the female plug 100. Also, the female
connecting portion 20 of the connector 1 is interchangeable
with the female connecting portion 150 of the tube member
140. Accordingly, the male connecting portion 110 of the
female plug 100 can be directly connected to the female
connecting portion 150 of the tube member 140 without the
connector 1 provided therebetween. In this case, although
not shown in the drawings, the male connecting portion 110
is connected to the female connecting portion 150 in a
similar manner to the connection of the male connecting
portion 110 to the female connecting portion 20 and the connection of the male connecting portion 50 to the female
connecting portion 150. That is to say, the female thread 116
of the male connecting portion 110 is screwed to the male
thread 156 of the female connecting portion 150 by inserting
the male member 111 of the male connecting portion 110
into the female connecting portion 150 and rotating the
female plug 100 relative to the tube member 140. The male
tapered surface 112 of the male member 111 comes into
surface contact with the female tapered surface 152 of the
female connecting portion 150, and thus, the two tapered
surfaces are taper-fitted to each other.

When the male connecting portion 110 of the female plug
100 is directly connected to the female connecting portion
150 of the tube member 140, the following problems arise.

First, if the female thread 116 is strongly screwed to the
male thread 156, the screwing structure (the female thread
116 or the male thread 156) may be damaged. To connect the
female plug 100 to the tube member 140, it is necessary to
screw the female thread 116 to the male thread 156 by
rotating the female plug 100 relative to the tube member 140
in a direction (tightening direction) in which the female
thread 116 is screwed to the male thread 156. The rotational
force applied at this time may vary from operator to opera-
tor. If a rotational force greater than necessary is applied in
the tightening direction, the screwing structure (the female
thread 116 or the male thread 156) will be damaged.

Second, the screwed connection of the female thread 116
to the male thread 156 may unintentionally loosen. The
screwed connection of the female thread 116 to the male
thread 156 can resist a pulling force, but will easily loosen
if a rotational force acting in a direction (loosening direc-
tion) in which the screwed connection is loosened is applied
to the female plug 100 or the tube member 140. A rotational
force acting in the loosening direction can be generated by,
for example, a twist in the tube 135. If the screwed connec-
tion of the female thread 116 to the male thread 156 loosens,
the male tapered surface 112 will be spaced apart from the
female tapered surface 152, resulting in leakage of the fluid
to the outside through a gap therebetween. When the fluid is
a hazardous drug solution (e.g., a drug solution containing
an anticancer drug), accidental drug exposure may occur.
When the fluid is a bodily fluid (e.g., blood) of a patient, a
near-miss event or a medical accident, such as blood leak-
age, may occur.

The above-described problems can be solved by connect-
ing the female plug 100 and the tube member 140 via the
connector 1. This will be further described below.

When using the connector 1, for example, the female
connecting portion 20 of the connector 1 is first connected
to the male connecting portion 110 of the female plug 100.
The female thread 116 is screwed to the male thread 26 by
rotating the female plug 100 in the tightening direction
relative to the first member 10. However, at this stage, the
two threads are loosely screwed together to such an extent
that taper fitting between the female tapered surface 22 and
the male tapered surface 112 is not complete. Next, the male
connecting portion 50 of the connector 1 is connected to the
female connecting portion 150 of the tube member 140. The
female thread 56 is screwed to the male thread 156 by
rotating the second member 40 in the tightening direction
relative to the tube member 140. However, at this stage, the
two threads are loosely screwed together to such an extent
that taper fitting between the female tapered surface 152 and
the male tapered surface 52 is not complete. Lastly, with the
female plug 100 held with one hand (e.g., the right hand) and
the tube member 140 held with the other hand (e.g., the left
hand), the female plug 100 is rotated in the tightening direction (clockwise direction when viewed from the female plug 100 side) relative to the tube member 140.

The rotational force acting in the tightening direction applied to the female plug 100 acts to rotate the first member 10 relative to the second member 40 in the direction indicated by arrow R1 in FIG. 7. The first member 10 rotates in the direction indicated by arrow R1 relative to the second member 40, and the side surface 15*a* of the engagement protrusion 15 collides with the side surface 45*a* of one of the divided sections of the second rib 45. The rotational force is transmitted from the engagement protrusion 15 to the second rib 45. The rotational force acting in the tightening direction applied to the female plug 100 is sequentially transmitted to the first member 10, the second member 40, and the tube member 140, causing the female thread 116 to be screwed to the male thread 26 and the female thread 56 to be screwed to the male thread 156. Thus, the male tapered surface 112 is taper-fitted to the female tapered surface 22, and the male tapered surface 52 is taper-fitted to the female tapered surface 152.

After the taper fitting between the female tapered surface 22 and the male tapered surface 112 and the taper fitting between the female tapered surface 152 and the male tapered surface 52 are complete, when an excessive rotational force acting in the tightening direction R1 is further applied to the first member 10 via the female plug 100, the engagement protrusion 15 is plastically deformed by the second rib 45. More specifically, a portion of the engagement protrusion 15 (a radially outer portion of the engagement protrusion 15) with which the second rib 45 collides is moved in the direction indicated by arrow R2 by the second rib 45 and accommodated in a radial gap 31 between the male connecting portion 11 and the second rib 45 on the side surface 15*b* side of the engagement protrusion 15. After that, the engagement protrusion 15 can move in the circumferential direction over the second rib 45. The engagement protrusion 15 is plastically deformed before any screwing structure (the female thread 116, the male thread 26, the female thread 56, or the male thread 156) is damaged. Therefore, the problem of the screwing structure (the female thread 116, the male thread 26, the female thread 56, or the male thread 156) being damaged by applying a rotational force greater than necessary in the tightening direction does not occur.

Once the engagement protrusion 15 is plastically deformed as described above, the engagement protrusion 15 can move over the second rib 45 in either of the direction indicated by arrow R1 and the direction indicated by arrow R2. Accordingly, after the engaging protrusion 15 has been plastically deformed, even when a rotational force acting in the direction (loosening direction) in which the screwed connection of the female thread 116 to the male thread 26 or the screwed connection of the female thread 56 to the male thread 156 loosens is applied to the female plug 100, the connector 1, or the tube member 140, the first member 10 rotates in the direction indicated by arrow R2 relative to the second member 40, and the rotational force is absorbed. As such, the rotational force acting in the loosening direction does not cause the male tapered surface 112 to be separated from the female tapered surface 22 or the male tapered surface 52 to be separated from the female tapered surface 152. Even when the fluid flowing through the connector 1 is a hazardous drug solution or a bodily fluid (e.g., blood) of a patient, a situation in which the hazardous drug solution or the bodily fluid leaks to the outside and causes accidental drug exposure or a medical accident such as blood leakage does not occur.

As described above, the connector 1 of Embodiment 1 is configured such that, when a rotational force of a predetermined value or greater is applied to the first member 10 in the tightening direction R1, the engagement protrusion 15 is plastically deformed by the second rib 45, and after that, the first member 10 can freely rotate (i.e., idly rotate) relative to the second member 40 in both the forward and reverse directions (the direction indicated by arrow R1 and the direction indicated by arrow R2). Therefore, even when an excessive rotational force acting in the tightening direction of the screwing structures (the female thread 116, the male thread 26, the female thread 56, and the male thread 156) is applied when connecting other members (the female plug 100 and the tube member 140) to the connector 1, any screwing structure will not be damaged. Moreover, even when a rotational force acting in the loosening direction of the screwing structures is applied to the connector 1 and the other members (the female plug 100 and the tube member 140) after the other members have been connected to the connector 1, the screwed connection between the screwing structures will not be unintentionally loosened.

There is no limitation on the method for selectively plastically deforming the engagement protrusion 15, out of the engagement protrusion 15 and the second rib 45, when a rotational force acting in the tightening direction R1 is applied to the first member 10. For example, (1) a method in which the second member 40 is made of a material that is stronger (or harder) than the material of the first member 10, (2) a method in which the first member 10 is made of a material with a higher level of toughness than the second member 40, (3) a method in which the engagement protrusion 15 is made smaller in circumferential length than each divided section of the second rib 45, and other methods can be employed.

The rotational force acting in the tightening direction R1 that is required for the engagement protrusion 15 to be plastically deformed by the second rib 45 and is applied to the first member 10 is not particularly limited, but is preferably 0.08 N·m or greater, more preferably 0.12 N·m or greater, and particularly preferably 0.15 N·m or greater. If the engagement protrusion 15 is plastically deformed by a rotational force smaller than this, it may be difficult to complete the taper fitting between the female tapered surface 22 and the male tapered surface 112 and the taper fitting between the male tapered surface 52 and the female tapered surface 152. That is to say, if the rotational force required to plastically deform the engagement protrusion 15 is equal to or greater than the above-described lower limit value, the taper fittings above can be reliably completed, and the likelihood of liquid leakage is reduced.

The rotational force required to plastically deform the engagement protrusion is set to a value less than a rotational force that would damage any screwing structure (the female thread 116, the male thread 26, the female thread 56, or the male thread 156). Specifically, the rotational force is, but is not particularly limited to, preferably 0.40 N·m or less, even more preferably 0.30 N·m or less, and particularly preferably 0.25 N·m or less.

The engagement protrusion 15 is plastically deformed by the second rib 45. The plastically deformed portion of the engagement protrusion 15 remains connected to the first member 10 without separating from the first member 10. Unlike Embodiment 1, if the engagement protrusion 15 is broken by the second rib 45 and a portion of the engagement protrusion 15 separates from the first member 10, the portion (separated portion) of the engagement protrusion 15 that has separated may freely move in the gap between the first member 10 and the second member 40 and obstruct the forward and reverse rotation of the first member 10 relative to the second member 40. If the separated portion obstructs the rotation of the first member 10 in the tightening direction R1, any screwing structure (the female thread 116, the male thread 26, the female thread 56, or the male thread 156) may be damaged. If the separated portion obstructs the rotation of the first member 10 in the loosening direction R2, the male tapered surface 112 may be spaced apart from the female tapered surface 22, or the male tapered surface 52 may be spaced apart from the female tapered surface 152.

The connector 1 of Embodiment 1 consists only of the two components; the first member 10 and the second member 40. Therefore, the connector 1 is constituted by a small number of components, and has a simple configuration. In addition, the connector 1 can be produced simply by producing the first member 10 and the second member 40 separately and then pushing the male connecting portion 11 of the first member 10 into the female connecting portion 41 of the second member 40. Therefore, the connector 1 is extremely easy to produce.

As shown in FIG. 7, in Embodiment 1, the side surfaces 15a and 15b of the engagement protrusion 15 are flat surfaces that are substantially parallel to the radial direction and parallel to the axis of the connector 1. Moreover, the side surfaces (or side surfaces of the grooves 46) 45a and 45b of the second rib 45 are flat surfaces that are substantially parallel to the radial direction and parallel to the axis of the connector 1. When the first member 10 rotates in the tightening direction R1, the side surface 15a of the engagement protrusion 15 abuts against the side surface 45a of one of the divided sections of the second ribs 45 so as to be in surface contact with each other. A large area of the engagement protrusion 15 abuts against the second rib 45. Therefore, a greater rotational force acting in the tightening direction R1 can be transmitted from the first member 10 to the second member 40. This is advantageous in completing the taper fitting between the female tapered surface 22 and the male tapered surface 112 and the taper fitting between the male tapered surface 52 and the female tapered surface 152.

In Embodiment 1, the male connecting portion 50 of the connector 1 is interchangeable with the male connecting portion 110 of the female plug 100. Also, the female connecting portion 20 of the connector 1 is interchangeable with the female connecting portion 150 of the tube member 140. Therefore, the male connecting portion 110 of the female plug 100 and the female connecting portion 150 of the tube member 140, which can be directly connected to each other, can be connected to each other via the connector 1 of Embodiment 1. It is possible to prevent damage to any screwing structure caused by an excessive rotational force acting in the tightening direction, and unintended loosening of the screwing structures, simply by connecting an existing female plug 100 and an existing tube member 140 to each other via the connector 1 without the need to modify them.

In the foregoing description, in a state in which the male connecting portion 110 of the female plug 100 is loosely connected to the female connecting portion 20 of the connector 1, and the female connecting portion 150 of the tube member 140 is loosely connected to the male connecting portion 50 of the connector 1, the female plug 100 is rotated in the tightening direction (clockwise direction when viewed from the female plug 100 side) relative to the tube member 140, to thereby screw the female thread 116 to the male thread 26 and the female thread 56 to the male thread 156 almost simultaneously. However, the connection method of the connector 1 is not limited to this. For example, one of the connection of the male connecting portion 110 to the female connecting portion 20 and the connection of the female connecting portion 150 to the male connecting portion 50 may be performed first (first-stage connection), followed by the other connection (second-stage connection). In this case, the application of a rotational force of a predetermined value or greater for causing the engagement protrusion 15 to be plastically deformed by the second rib 45 (i.e., the plastic deformation of the engagement protrusion 15) may be performed during the first-stage connection or the second-stage connection.

Embodiment 2

Figure 10:
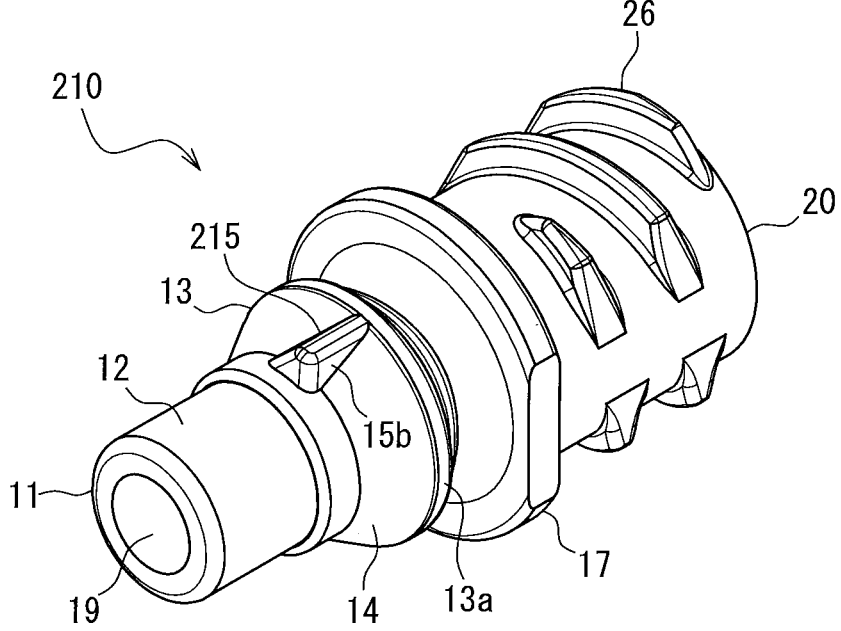
FIG. 10 is a perspective view of a first member constituting a medical connector according to Embodiment 2 of the present invention.

FIG. 10 is a perspective view of a first member 210 constituting a medical connector 2 according to Embodiment 2 of the present invention. Embodiment 2 is different from Embodiment 1 in terms of the shape of an engagement protrusion 215. The engagement protrusion 215 has a tapered, substantially triangular shape when viewed from the male connecting portion 11 side along the axis of the first member 210.

Figure 11:
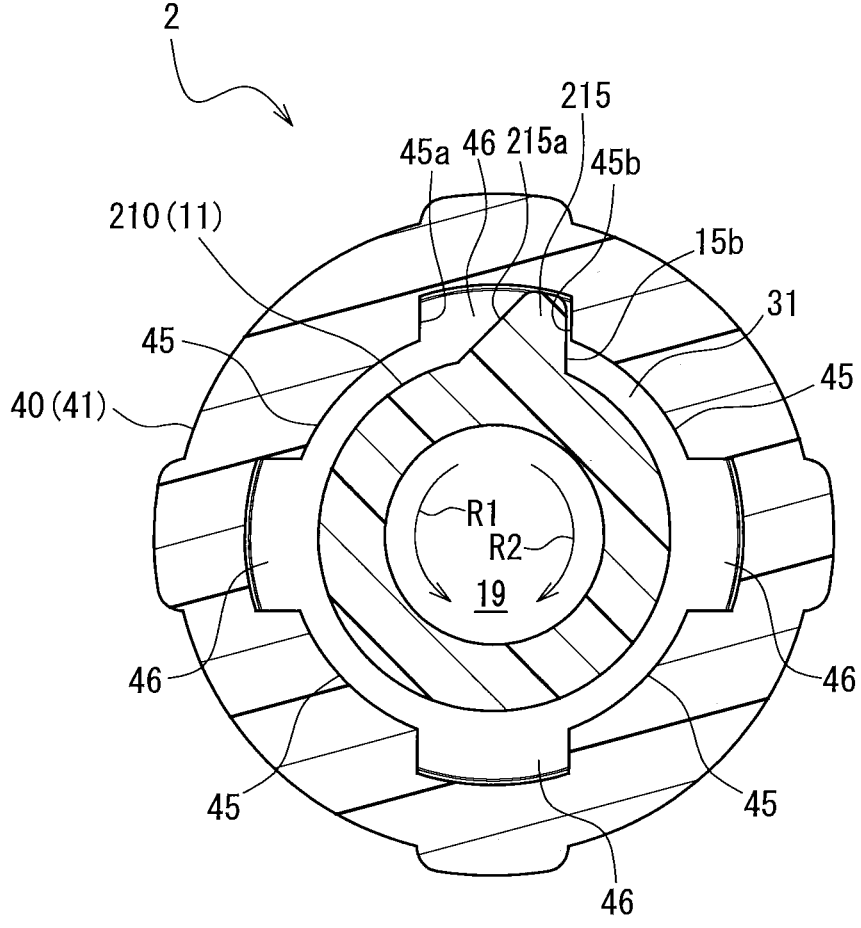
FIG. 11 is a cross-sectional view of the medical connector according to Embodiment 2 of the present invention, taken along a plane perpendicular to an axis thereof.

FIG. 11 is a cross-sectional view of the connector 2. As in FIG. 7 of Embodiment 1, the cross section in FIG. 11 passes through the engagement protrusion 215 and is perpendicular to the axis of the connector 2. The second member 40 of the connector 2 is the same as the second member 40 of Embodiment 1. A side surface 215a of the engagement protrusion 215 that opposes the side surface 45a of one of the divided sections of the second rib 45 in the circumferential direction is a flat surface that is inclined such that the distance from the side surface 45a increases radially outward. The side surface 15b of the engagement protrusion 215 that opposes the side surface 45b of another one of the divided sections of the second ribs 45 is a flat surface that is substantially parallel to the radial direction and parallel to the axis of the connector 2, as is the case with the side surface 15b of Embodiment 1 (see FIG. 7). The engagement protrusion 215 has a smaller length in the circumferential direction than the engagement protrusion 15 of Embodiment 1.

Figure 12:
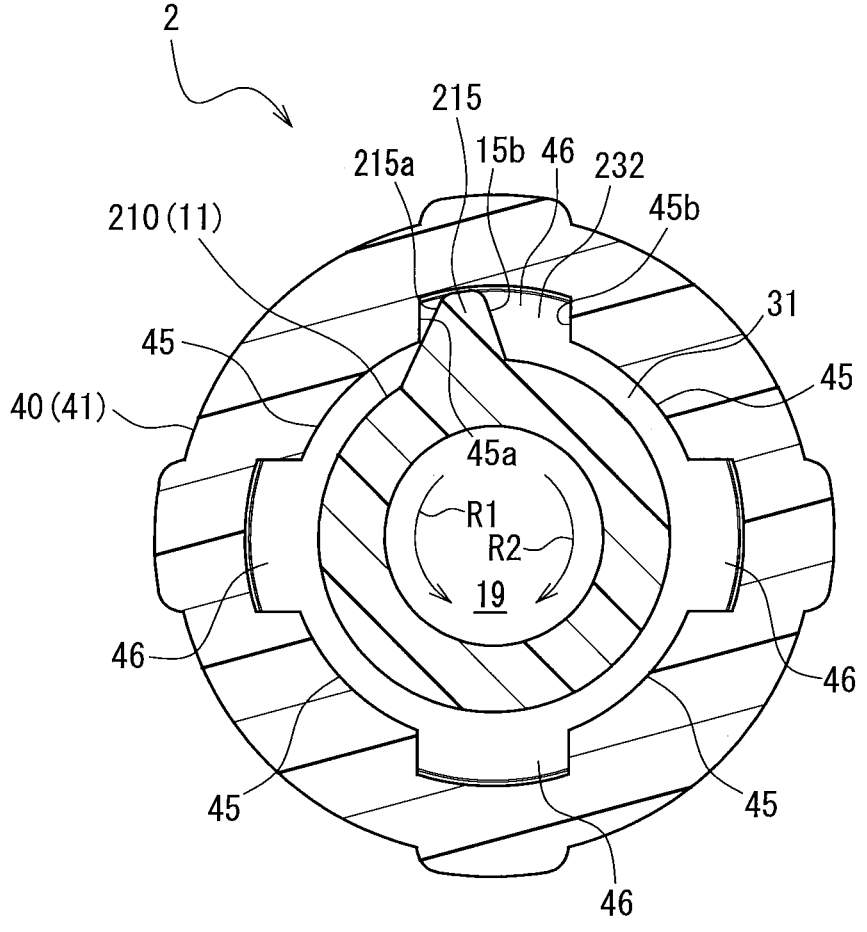
FIG. 12 is a cross-sectional view showing a state in which, in the medical connector according to Embodiment 2 of the present invention, a first engagement structure of the first member collides with a second engagement structure of a second member.

The connector 2 is used in a similar manner to that of the connector 1 of Embodiment 1. When a rotational force acting in the tightening direction, which is indicated by arrow R1, is applied to the first member 210, as can be seen from FIG. 12, the side surface 215a of the engagement protrusion 215 collides with the second rib 45, and the rotational force is transmitted from the engagement protrusion 215 to the second rib 45. When the side surface 215a collides with the second rib 45, the side surface 15b and the side surface 45b are widely spaced apart from each other in the circumferential direction, and thus, a gap 232 is formed therebetween.

When a greater rotational force acting in the tightening direction R1 is further applied to the first member 210, the engagement protrusion 215 is plastically deformed by the second rib 45. More specifically, a portion of the engagement protrusion 215 (a radially outer portion of the engagement protrusion 215) with which the second rib 45 collides is moved in the direction indicated by arrow R2 by the second rib 45. The above-described portion of the engagement protrusion 215 is moved into the gap 232 and can be deformed within the gap 232. As such, according to Embodiment 2, the gap 232 that is sufficient to allow for the plastic deformation of the engagement protrusion 215 is provided on the arrow R2 side with respect to the engagement protrusion 215. Therefore, the engagement protrusion 215 can be plastically deformed sufficiently and reliably. Furthermore, the volume of the portion of the engagement protrusion 215 that is plastically deformed is smaller than that of Embodiment 1, in which the substantially rectangular engagement protrusion 15 is provided. Therefore, the portion (deformed portion) of the engagement protrusion 215 that has been plastically deformed can be easily accommodated in the radial gap 31 between the male connecting portion 11 and the second rib 45. Even when the first member 210 rotates relative to the second member 40 in either of the direction indicated by arrow R1 and the direction indicated by arrow R2 after the engagement protrusion 215 has been plastically deformed, the engagement protrusion 215, or the deformed portion thereof, is unlikely to collide with the second rib 45. Therefore, the first member 210 easily idly rotate relative to the second member 40 after the engagement protrusion 215 has been plastically deformed. The likelihood of damage to any screwing structure that may occur when an excessive rotational force acting in the tightening direction of the screwing structures (the female thread 116, the male thread 26, the female thread 56, and the male thread 156) is applied when connecting other members (the female plug 100 and the tube member 140) to the connector 2 is further reduced. Moreover, the likelihood of unintentional loosening of the screwed connection between the screwing structures that may occur when a rotational force acting in the loosening direction of the screwing structures is applied after the other members (the female plug 100 and the tube member 140) have been connected to the connector 2 is further reduced.

The side surface 215a of the engagement protrusion 215 is inclined such that the distance from the side surface 45a of the second rib 45 increases radially outward. As can be understood from FIG. 12, the portion of the engagement protrusion 215 with which the second rib 45 collides is deformed radially inward. The plastically deformed portion of the engagement protrusion 215 is highly likely to be accommodated in the gap 31. This is advantageous in making it easier for the first member 210 to idly rotate in the forward and reverse directions relative to the second member 40 after the engagement protrusion 215 has been plastically deformed.

In Embodiment 2 described above, of the two side surfaces 215a and 15b of the engagement protrusion 215, the side surface 215a is inclined such that the distance from the side surface 45a of the second rib 45 increases radially outward; however, the present invention is not limited to this configuration. For example, the side surface 15b of the engagement protrusion 215 may be inclined such that the distance from the side surface 45b of the second rib 45 increases radially outward. In this case, the side surface 215a of the engagement protrusion 215 is a flat surface that is substantially parallel to the radial direction and parallel to the axis of the connector 2, as is the case with the side surface 15a of Embodiment 1 (see FIG. 7). When the first member 210 rotates in the tightening direction R1, the side surface 215a of the engagement protrusion 215 abuts against the side surface 45a of the second rib 45 so as to be in surface contact with each other, as in Embodiment 1. When the side surface 215a of the engagement protrusion 215 is a flat surface that is substantially parallel to the radial direction, compared to when the side surface 215a of the engagement protrusion 215 is an inclined surface that is inclined relative to the radial direction, a larger area of the engagement protrusion 215 abuts against the second rib 45, allowing a greater rotational force acting in the tightening direction R1 to be transmitted from the first member 210 to the second member 40. This is advantageous in completing the taper fitting between the female tapered surface 22 and the male tapered surface 112 and the taper fitting between the male tapered surface 52 and the female tapered surface 152. As in FIG. 12, when the side surface 215a collides with the second rib 45, a large gap is formed between the side surface 15b and the side surface 45b.

Embodiment 2 is the same as Embodiment 1 except for the above-described points. Descriptions of Embodiment 1 also apply to Embodiment 2.

Embodiment 3

Figure 13:
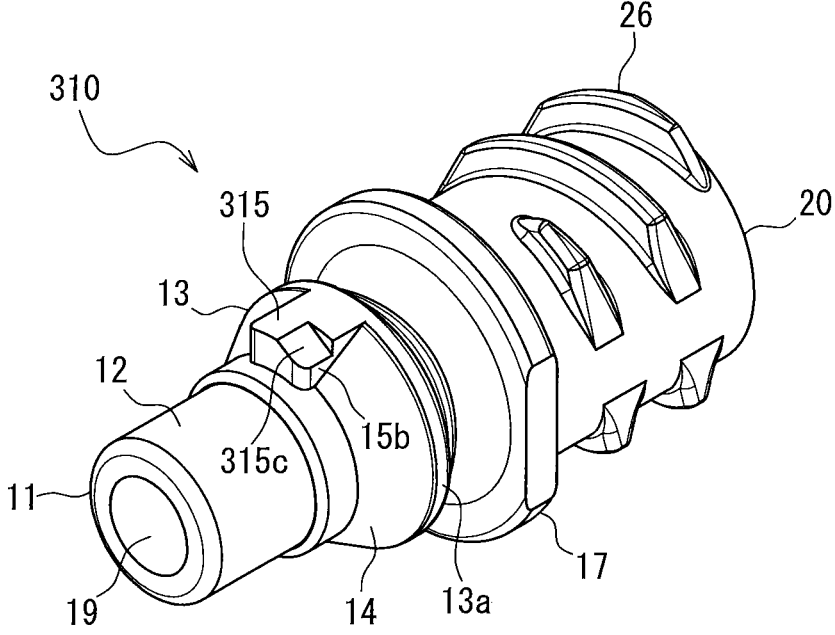
FIG. 13 is a perspective view of a first member constituting a medical connector according to Embodiment 3 of the present invention.

FIG. 13 is a perspective view of a first member 310 constituting a medical connector 3 according to Embodiment 3 of the present invention. Embodiment 3 is different from Embodiment 1 in terms of the shape of an engagement protrusion 315. As is the case with the engagement protrusion 15 of Embodiment 1, the engagement protrusion 315 has the side surfaces 15a and 15b. However, a cut-off portion 315c is formed in the engagement protrusion 315 by cutting off a protruding end-side (radially outer side) portion of the side surface 15b.

Figure 14:
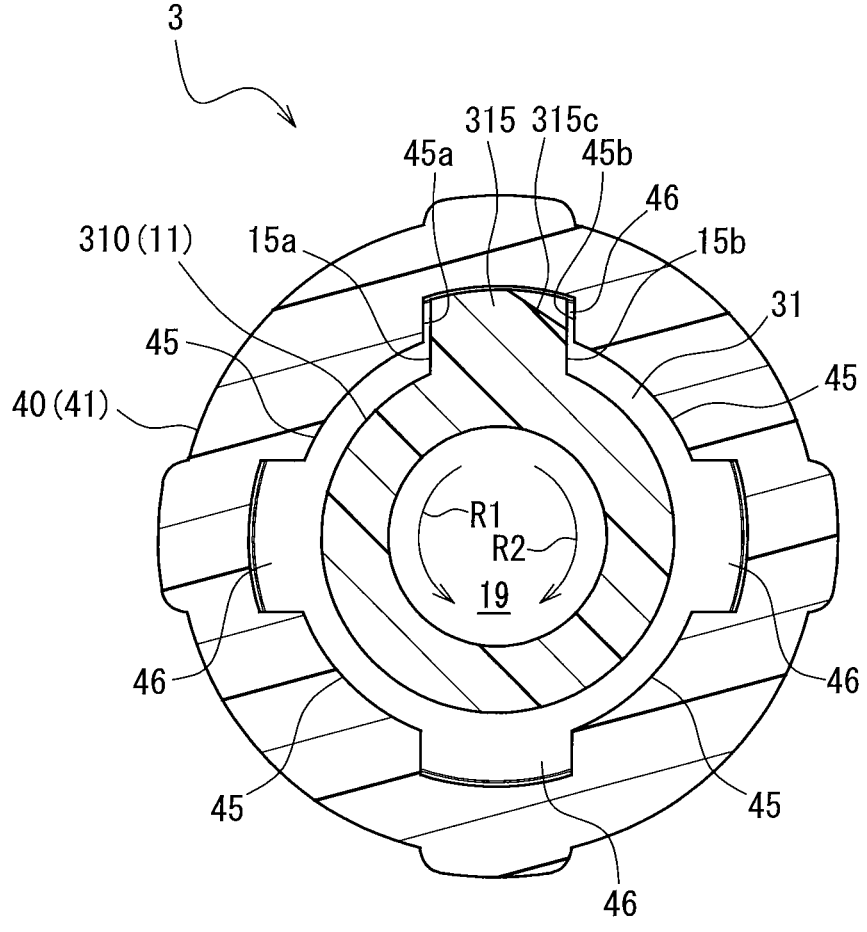
FIG. 14 is a cross-sectional view of the medical connector according to Embodiment 3 of the present invention, taken along a plane perpendicular to an axis thereof.

FIG. 14 is a cross-sectional view of the connector 3. As in FIG. 7 of Embodiment 1, the cross section in FIG. 14 passes through the engagement protrusion 315 and is perpendicular to the axis of the connector 3. The second member 40 of the connector 3 is the same as the second member 40 of Embodiment 1. The engagement protrusion 315 has a substantially trapezoidal shape when viewed from the male connecting portion 11 side along the axis of the first member 310. The cut-off portion 315c forms an inclined surface at a corner portion of the engagement protrusion 315 on the side surface 15b side, the inclined surface being inclined such that the distance to the side surface 15a decreases radially outward. The cut-off portion 315c is formed at a position that opposes the second rib 45 (side surface 45b) in the circumferential direction.

The connector 3 is used in a similar manner to that of the connector 1 of Embodiment 1. When a rotational force acting in the tightening direction, which is indicated by arrow R1, is applied to the first member 310, the side surface 15a of the engagement protrusion 315 collides with the side surface 45a of one of the divided sections of the second rib 45, and the rotational force is transmitted from the engagement protrusion 315 to the second rib 45, as in Embodiment 1.

When a greater rotational force acting in the tightening direction R1 is further applied to the first member 310, the engagement protrusion 315 is plastically deformed by the second rib 45. More specifically, a portion of the engagement protrusion 315 (a radially outer portion of the engagement protrusion 315) with which the second rib 45 collides is moved in the direction indicated by arrow R2 by the second rib 45. Since the cut-off portion 315c is formed at the protruding end of the side surface 15b of the engagement protrusion 315, the volume of the portion of the engagement protrusion 315 that is plastically deformed is smaller than that of Embodiment 1, in which the substantially rectangular engagement protrusion 15 is provided. Therefore, the portion (deformed portion) of the engagement protrusion 315 that has been plastically deformed can be easily accommodated in the radial gap 31 between the male connecting portion 11 and the second rib 45. Even when the first member 310 rotates relative to the second member 40 in either of the direction indicated by arrow R1 and the direction indicated by arrow R2 after the engagement protrusion 315 has been plastically deformed, the engagement protrusion 315, or the deformed portion thereof, is unlikely to collide with the second rib 45. Therefore, the first member 310 easily idly rotate relative to the second member 40 after the engagement protrusion 315 has been plastically deformed. The likelihood of damage to any screwing structure that may occur when an excessive rotational force acting in the tightening direction of the screwing structures (the female thread 116, the male thread 26, the female thread 56, and the male thread 156) is applied when connecting other members (the female plug 100 and the tube member 140) to the connector 3 is further reduced. Moreover, the likelihood of unintentional loosening of the screwed connection between the screwing structures that may occur when a rotational force acting in the loosening direction of the screwing structures is applied after the other members (the female plug 100 and the tube member 140) have been connected to the connector 3 is further reduced.

The cut-off portion 315c is formed on the side surface 15b, which is located on the opposite side to the side surface 15a with which the second rib 45 of the second member 40 collides when a rotational force acting in the tightening direction R1 is applied to the first member 310. The cut-off portion 315c forms a gap between the side surface 15b and the side surface 45b of the second rib 45. A portion of the engagement protrusion 315 with which the second rib 45 collides is moved into the gap formed by the cut-off portion 315c and can be deformed within the gap. Therefore, the engagement protrusion 315 can be plastically deformed sufficiently and reliably. This is advantageous in reducing the likelihood of the engagement protrusion 315 colliding with the second rib 45 even when the first member 310 rotates relative to the second member 40 in either of the direction indicated by arrow R1 and the direction indicated by arrow R2 after the engagement protrusion 315 has been plastically deformed.

Embodiment 3 is the same as Embodiment 1 except for the above-described points. Descriptions of Embodiment 1 also apply to Embodiment 3.

Embodiment 4

Figure 15:
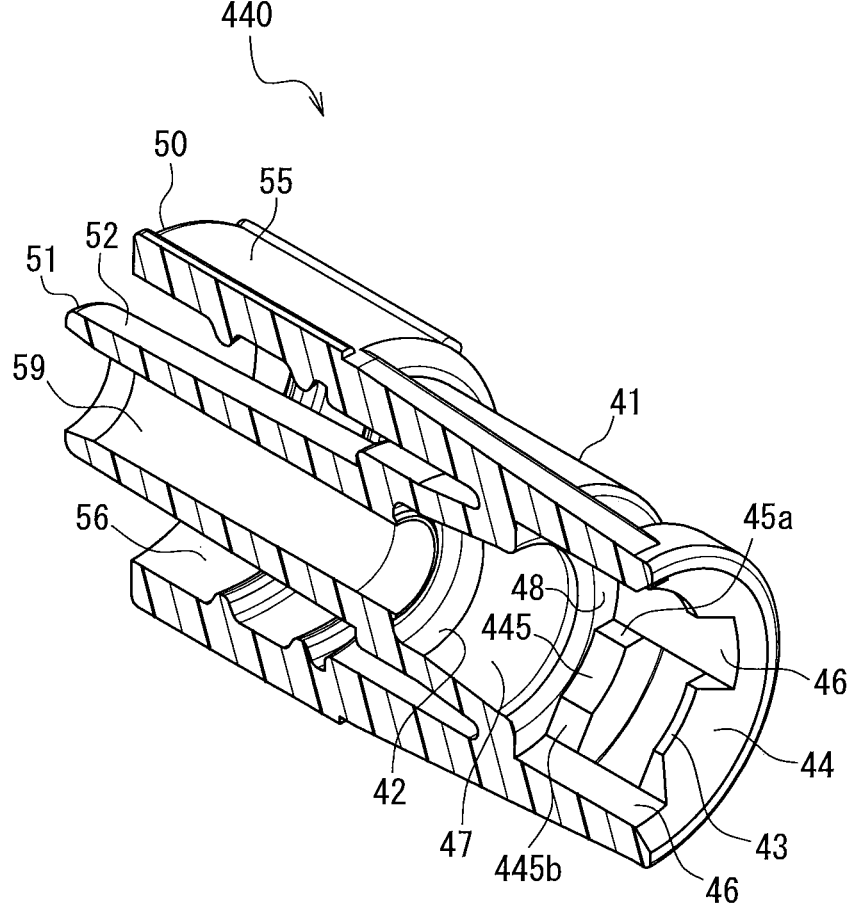
FIG. 15 is a cross-sectional perspective view of a second member constituting a medical connector according to Embodiment 4 of the present invention.

FIG. 15 is a cross-sectional perspective view of a second member 440 constituting a medical connector 4 according to Embodiment 4 of the present invention. Embodiment 4 is different from Embodiment 1 in terms of the shape of a second rib 445. As can be understood by comparing FIG. 15 with FIG. 5, in Embodiment 4, side surfaces 445b of the second rib 445 are inclined.

Figure 16:
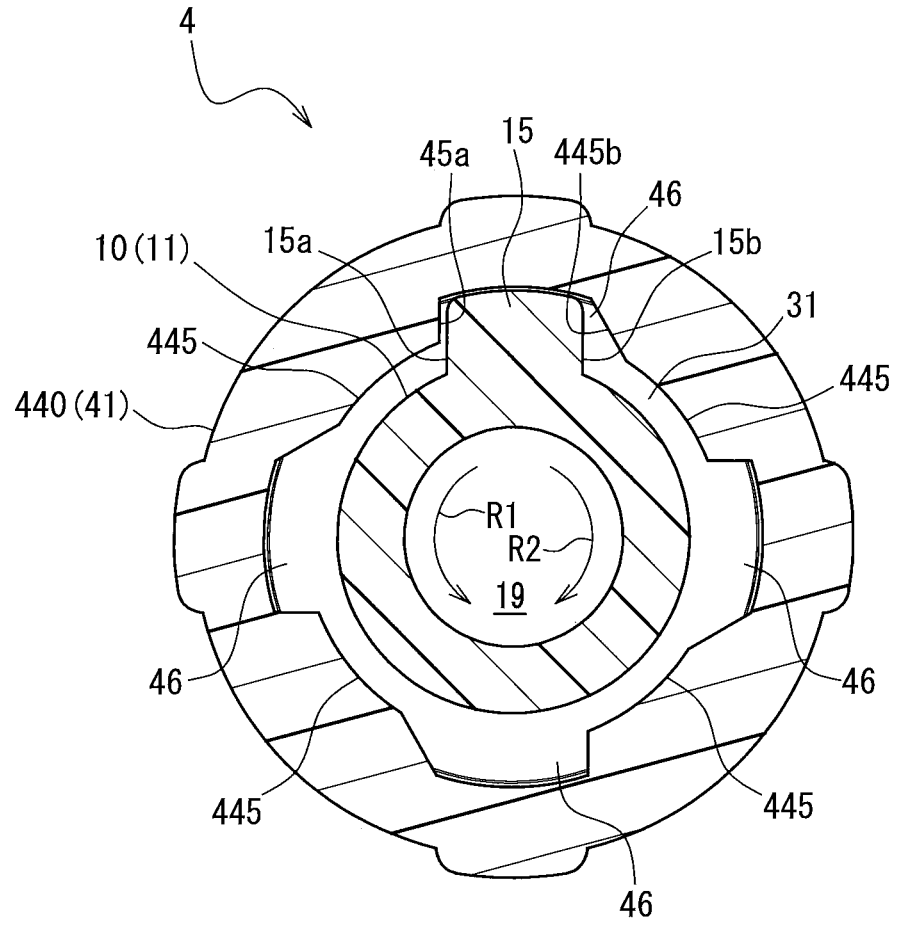
FIG. 16 is a cross-sectional view of the medical connector according to Embodiment 4 of the present invention, taken along a plane perpendicular to an axis thereof.

FIG. 16 is a cross-sectional view of the connector 4. As in FIG. 7 of Embodiment 1, the cross section in FIG. 16 passes through the engagement protrusion and is perpendicular to the axis of the connector 4. The first member 10 of the connector 4 is the same as the first member 10 of Embodiment 1. The side surface 445b of one of the divided sections of the second rib 445 that opposes the side surface 15b of the first rib 15 in the circumferential direction is a flat surface that is inclined such that the distance from the side surface 15b increases radially inward.

The connector 4 is used in a similar manner to that of the connector 1 of Embodiment 1. When a rotational force acting in the tightening direction, which is indicated by arrow R1, is applied to the first member 10, as can be seen from FIG. 16, the side surface 15a of the engagement protrusion 15 collides with the side surface 45a of the second rib 445, and the rotational force is transmitted from the engagement protrusion 15 to the second rib 445.

When a greater rotational force acting in the tightening direction R1 is further applied to the first member 10, the engagement protrusion 15 is plastically deformed by the second rib 445. More specifically, a portion of the engagement protrusion 15 (a radially outer portion of the engagement protrusion 15) with which the second rib 45 collides is moved in the direction indicated by arrow R2 by the second rib 445 and accommodated in the radial gap 31 between the male connecting portion 11 and the second rib 445 on the side surface 15b side of the engagement protrusion 15. The foregoing is the same as Embodiment 1.

When the first member 10 is rotated relative to the second member 440 in the loosening direction R2 after the engagement protrusion 15 has been plastically deformed, the engagement protrusion 15 first moves on the side surface 445b of the second rib 445. If the plastic deformation of the engagement protrusion 15 is insufficient, a portion (protruding portion) of the engagement protrusion 15 that protrudes radially outward may possibly collide with the side surface 445b. In that case, the protruding portion moves on the second rib 445 while being pressed against radially inward by the side surface 445b. Therefore, the engagement protrusion 15 can easily move over the second rib 445 in the direction indicated by arrow R2.

As such, according to Embodiment 4, a situation is unlikely to occur in which, when the first member 10 rotates in the loosening direction R2 after the engagement protrusion 15 has been plastically deformed, the rotation of the first member 10 in the loosening direction R2 is obstructed due to the engagement protrusion 15 colliding with the second rib 445. The first member 10 easily idly rotate relative to the second member 440 in the loosening direction R2 after the engagement protrusion 15 has been plastically deformed. Moreover, the likelihood of unintentional loosening of the screwed connection between the screwing structures that may occur when a rotational force acting in the loosening direction of the screwing structures (the female thread 116, the male thread 26, the female thread 56, and the male thread 156) is applied after the other members (the female plug 100 and the tube member 140) have been connected to the connector 4 is further reduced.

Embodiment 4 is the same as Embodiment 1 except for the above-described points. Descriptions of Embodiment 1 also apply to Embodiment 4.

In the connectors 2 and 3 of Embodiments 2 and 3 described above, the second rib 45 may be replaced with the second rib 445 of Embodiment 4. In this case, similar effects to those of Embodiment 4 can be achieved.

Embodiment 5

Figure 17:
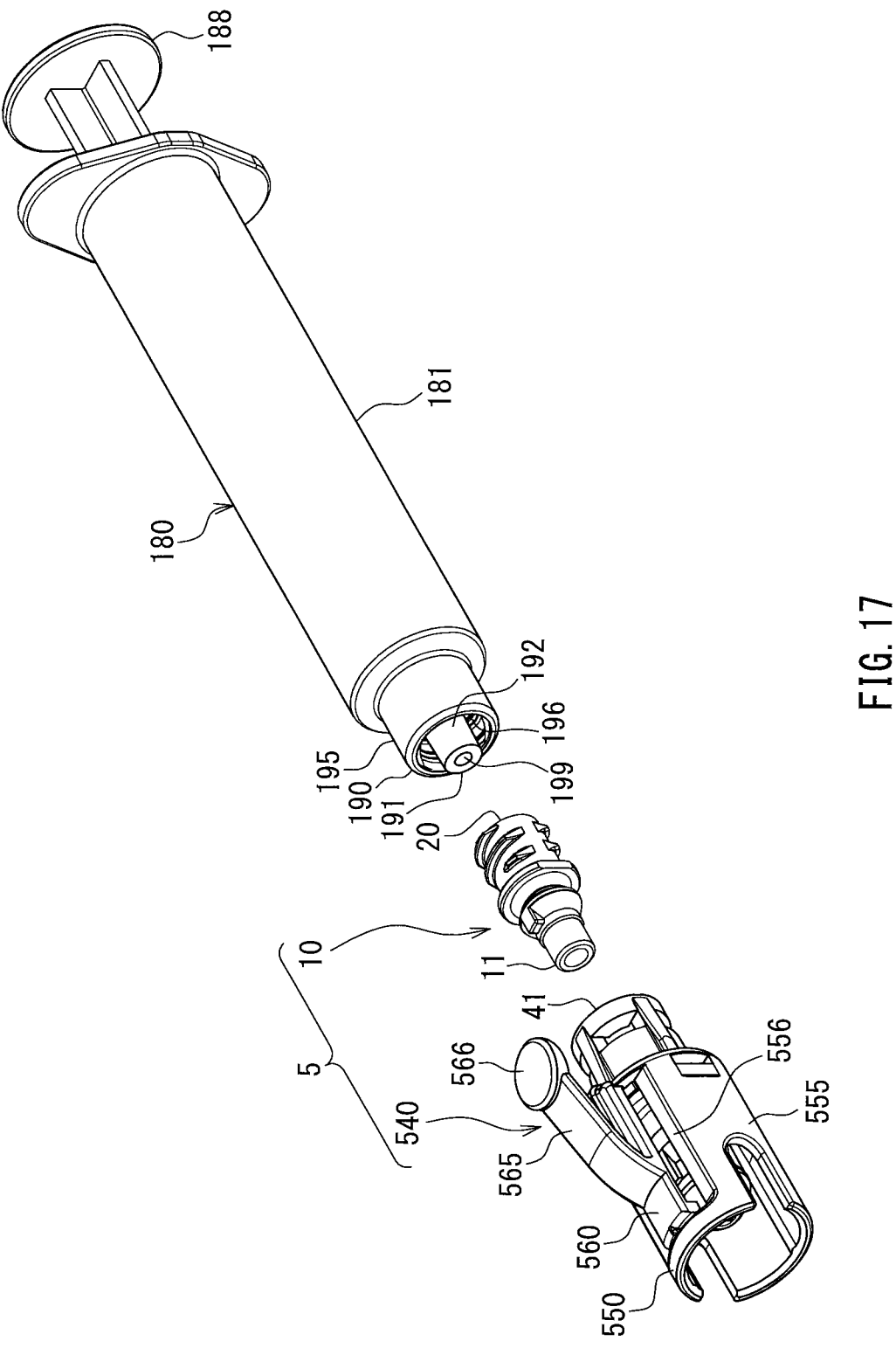
FIG. 17 is an exploded perspective view of a medical connector according to Embodiment 5 of the present invention.

FIG. 17 is an exploded perspective view of a medical connector 5 according to Embodiment 5 of the present invention. The connector 5 is constituted by the first member 10 and a second member 540. The connector 5 is used while being connected to a tube end 190 of a syringe 180. The first member 10 is the same as the first member 10 (see FIGS. 1 and 2) constituting the connector 1 of Embodiment 1. The second member 540 has a female connecting portion (first female connecting portion) 41 at a first end and a male connecting portion (second male connecting portion) 550 at a second end, the male connecting portion 550 being coaxial with the female connecting portion 41. The female connecting portion 41 is the same as the female connecting portion 41 constituting the connector 1 of Embodiment 1. The connector 5 is different from the connector 1 of Embodiment 1 in terms of the configuration of the male connecting portion 550.

Figure 18:
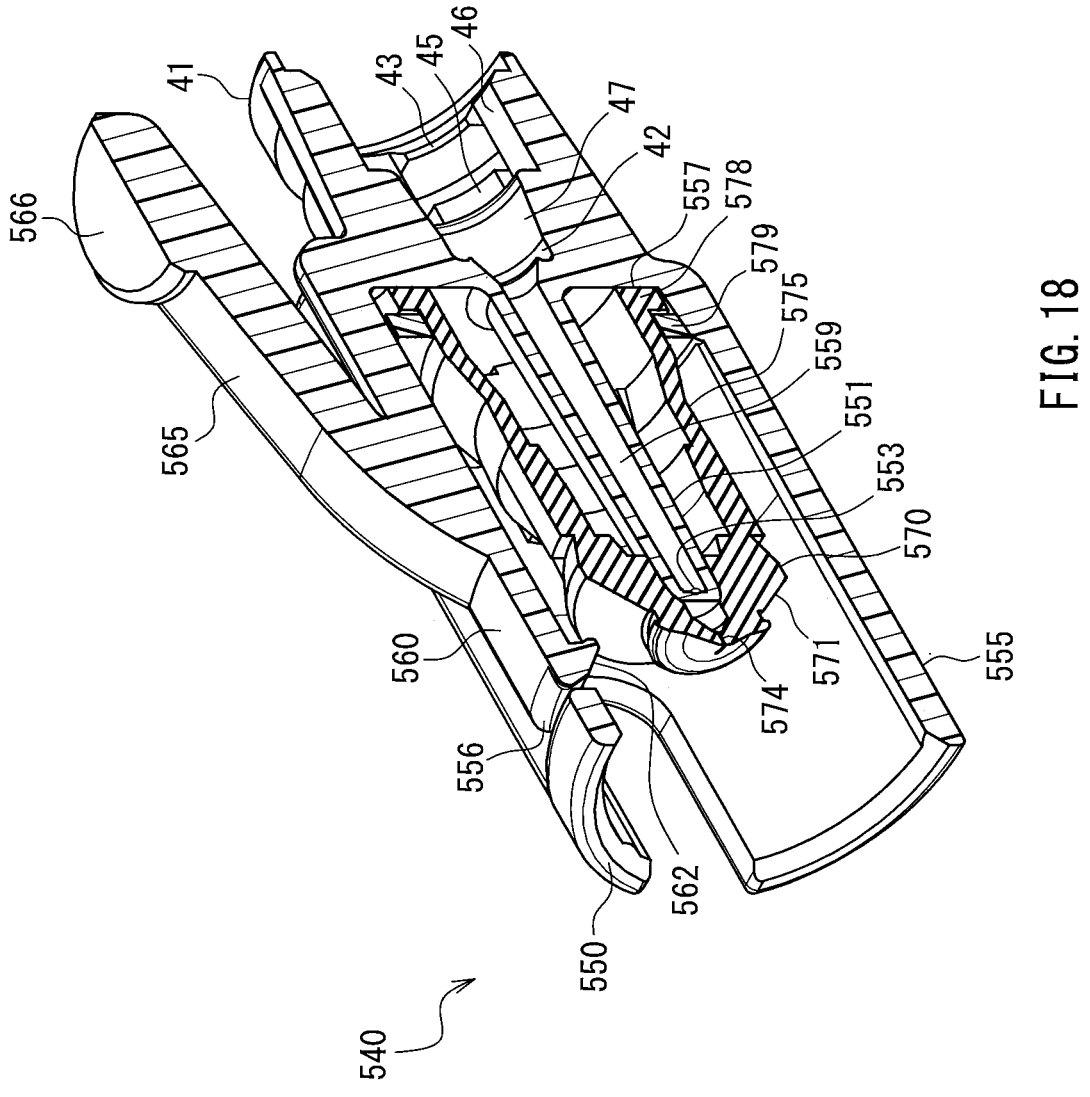
FIG. 18 is a cross-sectional perspective view of a second member constituting the medical connector according to Embodiment 5 of the present invention.

FIG. 18 is a cross-sectional perspective view of the second member 540. The male connecting portion 550 includes a male member 551, a hood 555, and a lever 560.

The male member 551 is a straight rod-shaped member. A flow path 559 is formed in the male member 551 and extends in the longitudinal direction of the male member 551. The flow path 559 is in communication with the inner cavity of the female connecting portion 41 (in particular, the second sealing surface 42 and the guide surface 47). Two lateral holes 553 (see FIG. 20, which will be described later) that are in communication with the flow path 559 are formed at respective positions near a distal end 552 of the male member 551. The two lateral holes 553 extend in the direction of the diameter of the male member 551.

A flange 557 extends outward in the radial direction from a base end of the male member 551. The flange 557 is a substantially circular plate-like member. The female connecting portion 41 is provided on a side surface of the flange 557 that is located opposite to the male member 551.

The hood 555 and the lever 560 extend toward the same side as the male member 551 from an outer circumferential edge of the flange 557. The hood 555 has a substantially cylindrical shape and is disposed coaxially with the male member 51 while being spaced apart from the male member 551 in the radial direction. An opening 556 (see FIG. 17) penetrating the hood 555 in the radial direction is formed in the hood 555. The lever 560 is disposed in the opening 556.

The lever 560 opposes the male member 551 in the radial direction. The lever 560 has an elongated thin plate-like shape (strip-like shape), and its longitudinal direction is substantially parallel to the longitudinal direction of the male member 551. The lever 560 has a cantilever structure, with its fixed end (base end) being fixed to the flange 557. A claw 562 protruding toward the male member 551 is provided at or near a free end (distal end) of the lever 560. An operating arm 565 protrudes outward (toward the opposite side to the male member 551) from a surface of the lever 560 that is located on the opposite side to the male member 551. The operating arm 565 extends from a position between the fixed end and the free end of the lever 560 beyond the fixed end of the lever 560 (or the flange 557) toward the female connecting portion 41 while being spaced apart from the lever 560.

The operating arm 565 has a mechanical strength that is high enough for the operating arm 565 to be considered as a substantially rigid body. On the other hand, the lever 560 can elastically bend and deform. The lever 560 can swing in a plane containing the axis of the second member 540. For example, when a force acting inward in the radial direction is applied to the operating portion 566 at the distal end of the operating arm 565, the lever 560 elastically bends and deforms so that the claw 562 moves away from the male member 551 substantially in the radial direction.

The male connecting portion 550 including the male member 551 and the lever 560 provided with the claw 562 is known as a male connector with a lever lock mechanism (e.g., FIGS. 4 to 6 of Patent Document 3). The male connecting portion 550 of Embodiment 5 has a single lever 560, but may also have a plurality of levers (e.g., FIGS. 2A to 2G of Patent Document 2).

The male connecting portion 550 further includes a shield 570. The shield 570 is disposed within the hood 555 so as to cover the male member 551. The shield 570 includes a head portion 571, a circumferential wall 575, and a base portion 578 in this order. The shield 570 is made of an elastic (or flexible) soft material (so-called elastomer) so that it can be relatively easily deformed by an external force and immediately recover to a state before deformation (initial state) when the external force is removed. Examples of soft materials that can be used include, but are not limited to, soft polyvinyl chloride, thermoplastic elastomers, and rubbers.

The head portion 571 has an inner cavity that is in communication with an inner space of the circumferential wall 575. A slit 574 penetrating the head portion 571 in the axial direction is formed at the innermost portion of the inner cavity. The slit 574 is a straight line-shaped cut portion having a "−" (minus sign) shape in a plan view. The distal end and its neighboring portion of the male member 551 are inserted into the inner cavity. An inner circumferential surface of the inner cavity is expanded in diameter by the male member 551 and is in surface contact with an outer circumferential surface of the male member 551. The lateral holes 553 of the male member 551 are closed by the inner circumferential surface of the inner cavity in a liquid-tight manner.

The entire circumferential wall 575 has a hollow tubular shape. The circumferential wall 575 is configured such that, when a compressive force acting in the axial direction (longitudinal direction of the male member 551) is applied to the shield 570, the circumferential wall 575 is elastically compressively deformed such that its axial length is reduced, and when released from the compressive force, the circumferential wall 575 immediately returns to the initial state. When the circumferential wall 575 is compressively deformed, the male member 551 passes through the slit 574 in the head portion 571, and a distal end portion of the male member 551 that includes the lateral holes 553 protrudes to the outside of the shield 570.

The base portion 578 protrudes outward in the radial direction from a lower end of the circumferential wall 575. The base portion 578 is placed on the flange 557, and an annular fixing ring 579 is put on the base portion 578. The fixing ring 579 is locked to an inner circumferential surface of the hood 555.

The male connecting portion 550 is not limited to the shield 570 of Embodiment 5, and may include any known shield (e.g., Patent Documents 4 and 5). Also, the male connecting portion 550 does not need to include the shield 570.

In FIG. 17, as in Embodiment 1, the connector 5 is assembled by inserting the male connecting portion 11 of the first member 10 into the female connecting portion 41 of the second member 540.

The female connecting portion 20 of the first member 10 of the assembled connector 5 is connected to the tube end (third male connecting portion) 190 of the syringe 180. The syringe 180 includes a hollow cylindrical barrel 181 and a plunger 188 that can be removably inserted into the barrel 181. The tube end 190 is provided at a distal end of the barrel 181. The tube end 190 has a male member 191 having a hollow cylindrical shape and an outer cylinder 195 surrounding the male member 191.

A flow path 199 extends through the male member 191. The flow path 199 is in communication with an inner cavity (liquid reserving portion) of the barrel 181 into which the plunger 188 can be removably inserted. An outer circumferential surface of the male member 191 has a male tapered surface (e.g., a 6% tapered surface) 192 whose outer diameter gradually decreases toward a distal end of the male member 191. The outer cylinder 195 has a substantially cylindrical shape and is disposed coaxially with the male member 191 while being spaced apart from the male member 191 in the radial direction. A female thread 196 is provided on an inner circumferential surface of the outer cylinder 195 that opposes the male member 191. The female thread 196 is a right-hand thread. The tube end 190 (in particular, the male tapered surface 192 and the female thread 196) may comply with ISO 594-2 or ISO 80369-7, for example. The tube end 190 is interchangeable with the male connecting portion 110 (see FIGS. 8 and 9) of the female plug 100 described in Embodiment 1.

Figure 19:
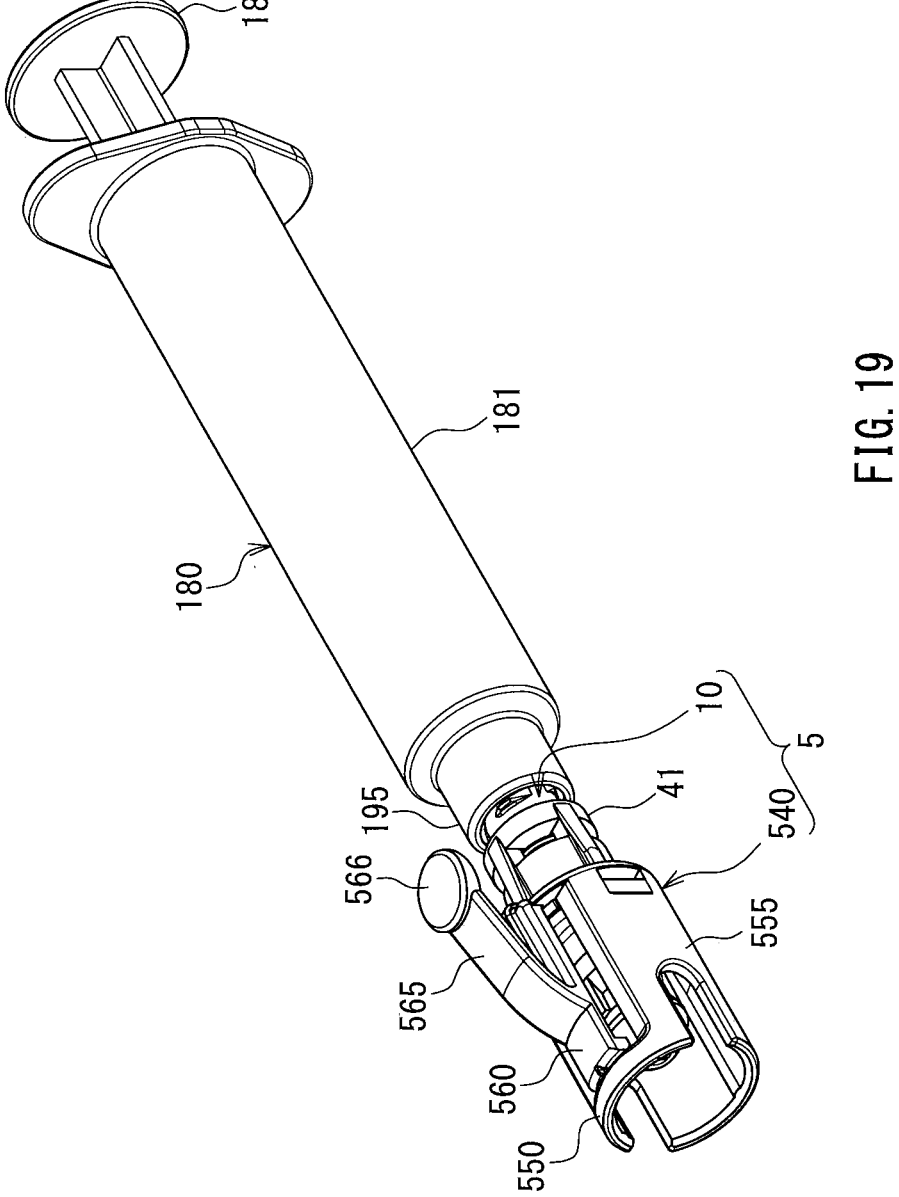
FIG. 19 is a perspective view of the medical connector according to Embodiment 5 of the present invention when connected to a syringe.
Figure 20:
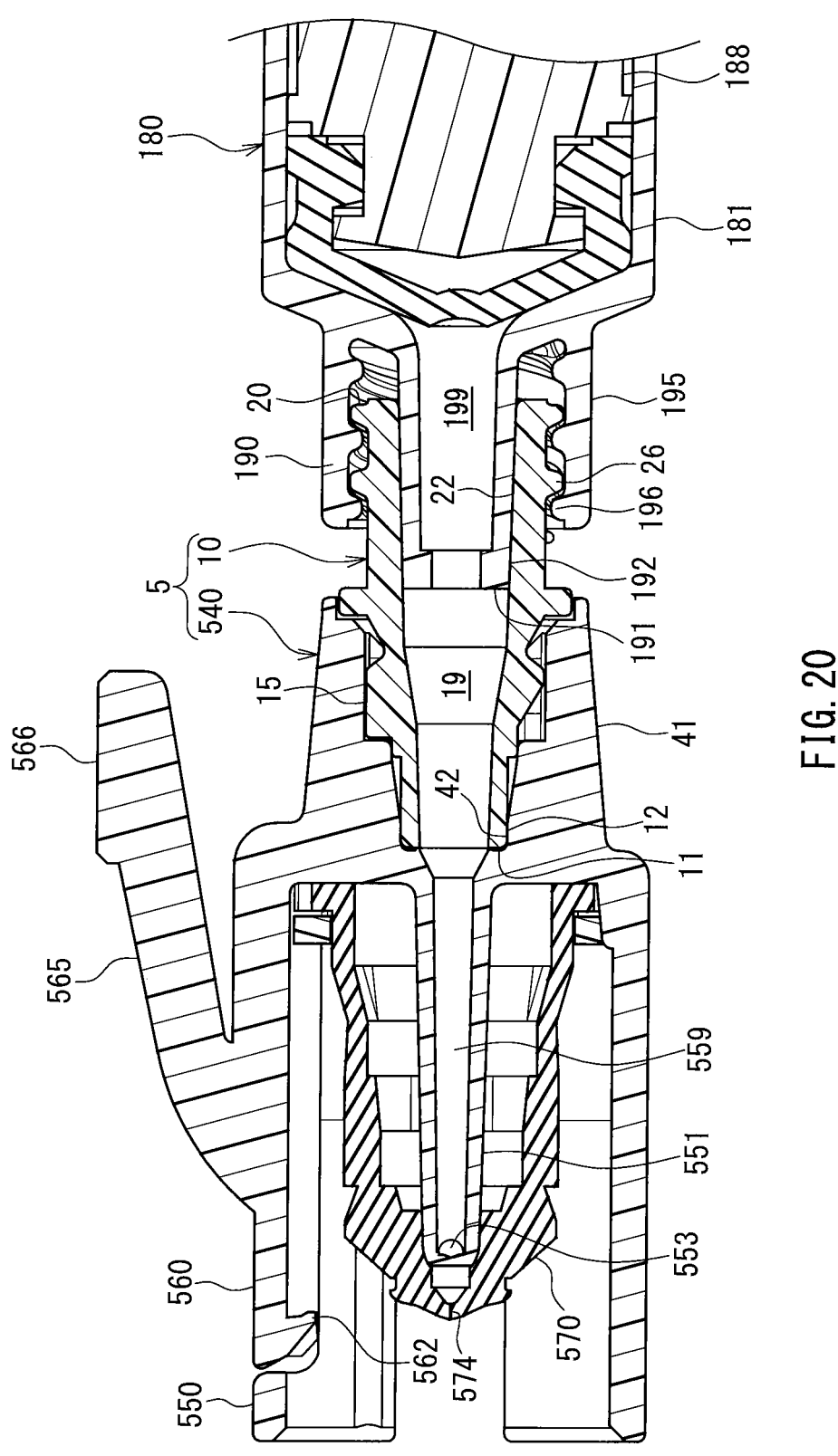
FIG. 20 is an enlarged cross-sectional view of the medical connector according to Embodiment 5 of the present invention when connected to the syringe.

FIG. 19 is a perspective view of the connector 5 connected to the syringe 180. FIG. 20 is a partial enlarged cross-sectional view thereof.

As shown in FIG. 20, the tube end 190 of the syringe 180 is connected to the first member 10 of the connector 5. The connection of the tube end 190 of the syringe 180 to the female connecting portion 20 of the first member 10 is the same as the connection of the male connecting portion 110 of the female plug 100 to the female connecting portion 20 of the first member 10, which has been described in Embodiment 1. That is to say, the male member 191 of the tube end 190 is inserted into the female connecting portion 20. The female connecting portion 20 is inserted into a gap between the male member 191 and the outer cylinder 195 of the tube end 190. The female thread 196 of the tube end 190 is screwed to the male thread 26 of the female connecting portion 20 by rotating the syringe 180 relative to the first member 10. The male tapered surface 192 of the male member 191 comes into surface contact with the female tapered surface 22 of the female connecting portion 20, and thus, the two tapered surfaces are taper-fitted to each other. The screwed connection of the female thread 196 to the male thread 26 prevents unintentional separation of the tube end 190 from the female connecting portion 20 even when a pulling force is applied.

Thus, the syringe 180 (flow path 199) and the connector 5 (flow paths 19 and 559) are in communication with each other. The male connecting portion 550 of the connector 5 can be connected to any female connecting portion (third female connecting portion, which is not shown). The third female connecting portion may be a female port portion having the same configuration as the female port portion 120 (see FIGS. 8 and 9) of the female plug 100, for example. The male member 551 is inserted into a septum (a member corresponding to the septum 123 of the female port portion 120) of that female port portion. The claw 562 engages with an engagement portion (e.g., a step corresponding to the step 103 in FIGS. 8 and 9) formed on an outer circumferential surface of the female port portion. In a state in which the male connecting portion 550 is connected to the female port portion, a fluid in the syringe 180 can be injected into the female port portion via the connector 5, and a fluid can also be suctioned from the female port portion into the syringe 180 via the connector 5.

Like the connector 1 of Embodiment 1, the connector 5 achieves the following effects.

In order to connect the connector 5 to the tube end 190 of the syringe 180, it is necessary to screw the female thread 196 of the tube end 190 to the male thread 26 of the female connecting portion 20. That is to say, with the syringe 180 (in particular, the barrel 181 thereof) held with one hand (e.g., the right hand) and the second member 540 held with the other hand (e.g., the left hand), the syringe 180 is rotated in the tightening direction (clockwise direction when viewed from the syringe 180 side) relative to the second member 540.

The connection structure between the male connecting portion 11 of the first member 10 and the female connecting portion 41 of the second member 540 of the connector 5 is the same as that of Embodiment 1. The rotational force acting in the tightening direction applied to the syringe 180 acts to rotate the first member 10 relative to the second member 540 in the direction indicated by arrow R1 in FIG. 7. The side surface 15*a* of the engagement protrusion 15 provided in the first member 10 collides with the side surface 45*a* of one of the divided sections of the second rib 45 provided in the second member 540. The rotation of the first member 10 in the tightening direction R1 is restricted, and the female thread 196 of the syringe 180 is screwed to the male thread 26 of the first member 10. The male tapered surface 192 of the syringe 180 is taper-fitted to the female tapered surface 22 of the first member 10.

After that, when a greater rotational force acting in the tightening direction R1 is further applied to the first member 10 via the syringe 180, the engagement protrusion 15 is plastically deformed by the second rib 45 as in Embodiment 1. After the engagement protrusion 15 has been plastically deformed, the engagement protrusion 15 can move in the circumferential direction over the second rib 45. The engagement protrusion 15 is plastically deformed before any screwing structure (the female thread 196 or the male thread 26) is damaged. Therefore, the problem of the screwing structure (the female thread 196 or the male thread 26) being damaged by applying a rotational force greater than necessary in the tightening direction does not occur.

Once the engagement protrusion 15 is plastically deformed as described above, the engagement protrusion 15 can move over the second rib 45 in either of the direction indicated by arrow R1 and the direction indicated by arrow R2. Accordingly, after the engaging protrusion 15 has been plastically deformed, even when a rotational force acting in the direction (loosening direction) in which the screwed connection of the female thread 196 to the male thread 26 loosens is applied to the syringe 180 or the second member 540, the first member 10 rotates relative to the second member 540 in the direction indicated by arrow R2, and the rotational force is thus absorbed. As such, the rotational force acting in the loosening direction does not cause the male tapered surface 192 to be separated from the female tapered surface 22. Even when the fluid flowing through the connector 5 is a hazardous drug solution or a bodily fluid (e.g., blood) of a patient, a situation in which the hazardous drug solution or the bodily fluid leaks to the outside and causes accidental drug exposure or a medical accident such as blood leakage does not occur.

As described above, the connector 5 of Embodiment 5 is configured such that, when a rotational force of a predetermined value or greater is applied to the first member 10 in the tightening direction R1, the engagement protrusion 15 is plastically deformed by the second rib 45, and after that, the first member 10 can freely rotate (i.e., idly rotate) relative to the second member 540 in both the forward and reverse directions (the direction indicated by arrow R1 and the direction indicated by arrow R2). Therefore, even when an excessive rotational force acting in the tightening direction of the screwing structures (the female thread 196 and the male thread 26) is applied when connecting the syringe 180 to the connector 5, any screwing structure will not be damaged. Moreover, even when a rotational force acting in the loosening direction of the screwing structures is applied to the connector 5 and the syringe 180 after the syringe 180 has been connected to the connector 5, the screwed connection between the screwing structures will not be unintentionally loosen.

Embodiment 5 is the same as Embodiment 1 except for the above-described points. Descriptions of Embodiment 1 also apply to Embodiment 5.

The first member 10 of the connector 5 may be provided with the engagement protrusion 215 of Embodiment 2, instead of the engagement protrusion 15. In this case, similar effects to those of Embodiment 2 can be achieved.

The first member 10 of the connector 5 may be provided with the engagement protrusion 315 of Embodiment 3, instead of the engagement protrusion 15. In this case, similar effects to those of Embodiment 3 can be achieved.

The second member 40 of the connector 5 may be provided with the second rib 445 of Embodiment 4, instead of the second rib 45. In this case, similar effects to those of Embodiment 4 can be achieved.

It should be understood that Embodiments 1 to 5 above are given by way of example only. The present invention is not limited to Embodiments 1 to 5 above, and modifications can be made thereto as appropriate.

The rotation prevention mechanism of the present invention includes a first engagement structure provided on a first member and a second engagement structure provided on a second member. In Embodiments 1 to 5 above, the first engagement structure is plastically deformable, and the second engagement structure is substantially not plastically deformable; however, the present invention is not limited to this configuration. A configuration may also be adopted in which the first engagement structure is substantially not plastically deformable, and the second engagement structure is plastically deformable. In addition, in Embodiments 1 to 5 above, the first engagement structure is provided on a first male connecting portion, and the second engagement structure is provided on a first female connecting portion; however, the present invention is not limited to this configuration. A configuration may also be adopted in which the first engagement structure is provided on the first female connecting portion, and the second engagement structure is provided on the first male connecting portion.

In Embodiments 1 to 5 above, the first male connecting portion 11 is provided in the first member, and the first female connecting portion 41 is provided in the second member; however, the present invention is not limited to this configuration. A configuration may also be adopted in which the first male connecting portion 11 is provided in the second member, and the first female connecting portion 41 is provided in the first member.

In Embodiments 1 to 5, the second female connecting portion 20 having the male thread 26 is provided at an end of the first member that is opposite to the second member; however, the present invention is not limited to this configuration. In the present invention, it is sufficient that a screwing structure is provided at the end of the first member that is opposite to the second member. The screwing structure is not limited to the male thread 26, and may be a female thread, for example. At the end of the first member that is opposite to the second member, a male connecting portion similar to the male connecting portion 50, or any connection structure having a screwing structure, may be provided instead of the second female connecting portion 20.

At an end of the second member that is opposite to the first member, the second male connecting portion 50 having the female thread 56 is provided in Embodiments 1 to 4, or the second male connecting portion 550 having the lever lock mechanism is provided in Embodiment 5; however, the present invention is not limited to this configuration. Any connection structure (e.g., a known male connecting portion or a known female connecting portion) may be provided at the end of the second member that is opposite to the first member. In this case, the connection structure may or may not have a configuration, such as a screwing structure or a lever lock mechanism, for maintaining the connected state. Alternatively, the end of the second member that is opposite to the first member may be integrally provided with, for example, a tube end of a syringe, a three-way stopcock, or the like, rather than a connection structure.

In the present invention, the "tightening direction" of screwing structures constituted by a male thread and a female thread means a direction in which the male thread or the female thread needs to be rotated in order to screw the male thread to the female thread. The "loosening direction" of screwing structures constituted by a male thread and a female thread means a direction in which the male thread or the female thread needs to be rotated in order to loosen the screwed connection between the male thread and the female thread. When screwing a male thread to a female thread, the direction of rotation of the male thread when the male thread is rotated relative to the female thread that is stationary and the direction of rotation of the female thread when the female thread is rotated relative to the male thread that is stationary are opposite when viewed from the same side (the male thread side or the female thread side). The same holds true when loosening the screwed connection between the male thread and the female thread. In the foregoing description, the directions of relative rotation between the first member and the second member are defined as follows: a direction in which the first member is rotated as indicated by arrow R1 relative to the second member that is stationary is defined as the "tightening direction", and a direction in which the first member is rotated as indicated by arrow R2 relative to the second member that is stationary is defined as the "loosening direction" (see FIGS. 7, 11, 14, and 16). These definitions are merely for the purpose of facilitating the understanding of the present invention. In the present invention, the second member is not necessarily always stationary. When the second member is rotated relative to the first member that is stationary, a direction in which the second member is rotated as indicated by arrow R1 is defined as the "loosening direction", and a direction in which the second member is rotated as indicated by arrow R2 is defined as the "tightening direction".

INDUSTRIAL APPLICABILITY

The present invention can be widely used in the medical field as a connector for forming a flow path for a fluid. Although there is no limitation on the fluid, the fluid is preferably a liquid, and particularly preferably a liquid (such as a drug solution, blood, or the like) that should be prevented from leaking to the outside.

DESCRIPTION OF REFERENCE NUMERALS

1, 2, 3, 4, 5 Connector (Medical connector)
10, 210, 310 First member
11 First male connecting portion
12 First sealing surface (Sealing mechanism)
13 Annular rib (Dislodgement prevention mechanism)
15, 215, 315 Engagement protrusion (First engagement structure, Rotation prevention mechanism)
15a, 215a Side surface of engagement protrusion
315c Cut-off portion in engagement protrusion

20 Second female connecting portion
26 Male thread (Screwing structure)
40, 440, 540 Second member
41 First female connecting portion
42 Second sealing surface (Sealing mechanism)
43 First rib (Dislodgement prevention mechanism)
45, 445 Second rib (Second engagement structure, Rotation prevention mechanism)
45a Side surface of second rib
445b Side surface of second rib
50, 550 Second male connecting portion
51,551 Male member
55 Outer cylinder
56 Female thread
560 Lever
562 Claw
110, 190 Male connecting portion (Third male connecting portion)
116, 196 Female thread (Other screwing structure)
150 Female connecting portion (Third female connecting portion)

The invention claimed is:

1. A medical connector comprising a first member and a second member,
wherein a male connecting portion is provided at one of a first end of the first member and a first end of the second member,
a female connecting portion is provided at the other of the first end of the first member and the first end of the second member,
a screwing structure is provided at a second end of the first member,
the male connecting portion is inserted into the female connecting portion, and the first member and the second member are in communication with each other,
the medical connector includes:
a dislodgement prevention mechanism that prevents the male connecting portion from dislodging from the female connecting portion;
a sealing mechanism that connects the male connecting portion and the female connecting portion to each other in a liquid-tight manner; and
a rotation prevention mechanism that prevents the first member from rotating relative to the second member,
the rotation prevention mechanism includes a first engagement structure provided on the first member, and a second engagement structure provided on the second member so as to be able to abut against the first engagement structure in a circumferential direction, and
when a direction in which another screwing structure that can be screwed to the screwing structure is rotated in order to screw the other screwing structure to the screwing structure is defined as a tightening direction, the rotation prevention mechanism is configured such that, when a rotational force of a predetermined value or greater is applied to the first member in the tightening direction, one of the first engagement structure and the second engagement structure is plastically deformed by the other, so that the first member can be rotated in both forward and reverse directions relative to the second member.

2. The medical connector according to claim 1,
wherein both a surface of the first engagement structure and a surface of the second engagement structure that collide with each other when a rotational force acting in the tightening direction is applied to the first member are flat surfaces that are substantially parallel to a radial direction.

3. The medical connector according to claim 1,
wherein the one that is to be plastically deformed, of the first engagement structure and the second engagement structure has a substantially rectangular shape when viewed along an axis of the connector.

4. The medical connector according to claim 1,
wherein the one that is to be plastically deformed, of the first engagement structure and the second engagement structure has a substantially triangular shape when viewed along an axis of the connector.

5. The medical connector according to claim 1,
wherein a corner portion of the one that is to be plastically deformed, of the first engagement structure and the second engagement structure is cut off, the corner portion being located on a side opposite to a side that abuts against the other of the first engagement structure and the second engagement structure when a rotational force acting in the tightening direction is applied to the first member.

6. The medical connector according to claim 1,
wherein a surface of the other of the first engagement structure and the second engagement structure is inclined relative to the circumferential direction, the surface being located on a side opposite to a surface against which the one that is to be plastically deformed, of the first engagement structure and the second engagement structure abuts when a rotational force acting in the tightening direction is applied to the first member.

7. The medical connector according to claim 1,
wherein the female connecting portion is a first female connecting portion,
the second end of the first member includes a tubular second female connecting portion and a male thread provided on an outer circumferential surface of the second female connecting portion, and
the screwing structure is the male thread.

8. The medical connector according to claim 1,
wherein the male connecting portion is a first male connecting portion, and
a second male connecting portion is provided at the second end of the second member, the second male connecting portion including a male member, an outer cylinder surrounding the male member, and a female thread provided on an inner circumferential surface of the outer cylinder.

9. The medical connector according to claim 1,
wherein the male connecting portion is a first male connecting portion,
the female connecting portion is a first female connecting portion,
a second male connecting portion is provided at one of the second end of the first member and a second end of the second member,
a second female connecting portion is provided at the other of the second end of the first member and the second end of the second member,
the second male connecting portion is interchangeable with a third male connecting portion that is connectable to the second female connecting portion, and
the second female connecting portion is interchangeable with a third female connecting portion that is connectable to the second male connecting portion.

10. The medical connector according to claim 1, wherein the male connecting portion is a first male connecting portion, and a second male connecting portion is provided at a second end of the second member, the second male connecting portion including a male member and a lever that is provided with a claw protruding toward the male member and is configured to be elastically rotatable so that the claw moves away from the male member.

11. The medical connector according to claim 1, wherein the rotational force of the predetermined value or greater is 0.08 N·m or greater.

12. The medical connector according to claim 1 wherein each of the first member and the second member is a single component made entirely of one material.

* * * * *